US012723073B2

(12) United States Patent
Lee et al.

(10) Patent No.: US 12,723,073 B2
(45) Date of Patent: Sep. 1, 2026

(54) USE OF M-CSF OR G-CSF FOR DIAGNOSIS OR TREATMENT OF PULMONARY FIBROSIS

(71) Applicant: FNCT BIOTECH, INC., Seoul (KR)

(72) Inventors: Su Jae Lee, Seoul (KR); Mi Young Choi, Seoul (KR); Jae Kyung Myung, Seoul (KR); Min Jung Kim, Seoul (KR); Hae June Lee, Seoul (KR)

(73) Assignee: FNCT BIOTECH, INC, Seoul (KR)

( * ) Notice: Subject to any disclaimer, the term of this patent is extended or adjusted under 35 U.S.C. 154(b) by 1434 days.

(21) Appl. No.: 17/426,905

(22) PCT Filed: Jan. 30, 2020

(86) PCT No.: PCT/KR2020/001404
§ 371 (c)(1),
(2) Date: Jul. 29, 2021

(87) PCT Pub. No.: WO2020/159243
PCT Pub. Date: Aug. 6, 2020

(65) Prior Publication Data

US 2025/0376515 A1 Dec. 11, 2025

(30) Foreign Application Priority Data

Jan. 30, 2019 (KR) ........................ 10-2019-0011843
Jan. 29, 2020 (KR) ........................ 10-2020-0010727

(51) Int. Cl.

| | |
|---|---|
| ***A61K 39/00*** | (2006.01) |
| ***A61P 11/00*** | (2006.01) |
| ***A61P 43/00*** | (2006.01) |
| ***C07K 16/24*** | (2006.01) |

(52) U.S. Cl.
CPC ............ *C07K 16/243* (2013.01); *A61K 39/00* (2013.01); *A61P 11/00* (2018.01); *A61P 43/00* (2018.01); *A61K 2039/505* (2013.01); *A61K 2039/507* (2013.01); *C07K 2317/76* (2013.01)

(58) Field of Classification Search
CPC ...................................................... A61K 39/00
See application file for complete search history.

(56) References Cited

FOREIGN PATENT DOCUMENTS

| | | | |
|---|---|---|---|
| CN | 101014386 | A | 8/2007 |
| CN | 102770456 | A | 11/2012 |
| EP | 3 050 570 | A1 | 8/2016 |
| EP | 3 778 917 | A2 | 2/2021 |
| KR | 10-2016-0137810 | A | 12/2016 |
| WO | 2015/028454 | A2 | 3/2015 |
| WO | 2015/028454 | A3 | 3/2015 |

OTHER PUBLICATIONS

Scalzo-Inguanti et al., vol. 102, Aug. 2017, Journal of Leukocyte Biology 537-549.*

Meziani et al., "CSF1R inhibition prevents radiation pulmonary fibrosis by depletion of interstitial macrophages", European Respiratory Journal, vol. 51, No. 3, Mar. 1, 2018 (13 pages total).

Zhao et al., "Pretreatment with G-CSF Could Enhance the Antifibrotic Effect of BM-MSCs on Pulmonary Fibrosis", Stem Cells International, vol. 2019, Article ID 1726743, Jan. 3, 2019 (13 pages total).

Zhao et al., "G-CSF Inhibits Pulmonary Fibrosis by Promoting BMSC Homing to the Lungs via SDF-1/CXCR4 Chemotaxis", Scientific Reports, vol. 10, No. 10515, Dec. 29, 2020 (11 pages total).

Written Opinion dated May 26, 2020 from the International Searching Authority in International Application No. PCT/KR2020/001404.

Extended European Search Report dated Nov. 3, 2022 from the European Patent Office in EP Application No. 20747785.2.

Communication dated Sep. 3, 2021 from the Korean Intellectual Property Office in Application No. 10-2021-0107637.

Xiaoping Ao et al., "Radiation produces differential changes in cytokine profiles in radiation lung fibrosis sensitive and resistant mice", Journal of Hematology & Oncology, Feb. 2, 2009, vol. 2, No. 6, pp. 1-12 (12 pages total).

Chinese Office Action dated Nov. 15, 2023 in Chinese Application No. 202080012031.2.

Meziani et al., "CSF1R inhibition prevents radiation pulmonary fibrosis by depletion of interstitial macrophages" Basic Science and Interstitial Lung Disease, 2018, vol. 51, pp. 1-13 (13 pages total).

Xu et al., "[Autoantibody against granulocyte-macrophage colony-stimulating factor and other serum markers in pulmonary alveolar proteinosis]"Chin J Tuberc Resipr Dis, Dec. 2004, vol. 27, No. 12, pp. 824-828 (6 pages total).

Liu, "Research advances in pulmonary alveolar proteinosis", Journal of Internal Medicine Concepts & Practice, 2016, vol. 11, Issue 4, 4 Pages total.

Jesus Banuelos, et al., "Granulocyte colony-stimulating factor blockade enables dexamethasone to inhibit lipopolysaccharide-induced murine lung neutrophils", PLOS One, May 19, 2017, pp. 1-16, vol. 12, (5).

(Continued)

*Primary Examiner* — Prema M Mertz
(74) *Attorney, Agent, or Firm* — Sughrue Mion, PLLC

(57) ABSTRACT

The present disclosure relates to a use of M-CSF or G-CSF for diagnosis or treatment of pulmonary fibrosis and, more specifically, to: a marker for diagnosing the level of development or progression of pulmonary fibrosis, comprising M-CSF and/or G-CSF; and a composition for preventing or treating pulmonary fibrosis, comprising an M-CSF inhibitor and a G-CSF inhibitor as active ingredients.

The present inventors have ascertained that M-CSF and/or G-CSF is a marker for development or progression of pulmonary fibrosis, and have confirmed that a composition, which comprises M-CSF and G-CSF and which binds to M-CSF and G-CSF so that the inherent mechanism thereof can be prevented, has an effect of significantly inhibiting myofibroblast hyperplasia or pulmonary fibrosis of the pulmonary cells, and thus the marker and the composition of the present disclosure are expected to be effectively usable for diagnosis, prevention or treatment of pulmonary fibrosis.

9 Claims, 27 Drawing Sheets

Specification includes a Sequence Listing.

(56) References Cited

OTHER PUBLICATIONS

Kenji Adachi et al., "Granulocyte colony-stimulating factor exacerbates the acute lung injury and pulmonary fibrosis induced by intratracheal administration of bleomycin in rats", Exp Toxic Pathol, 2002, pp. 501-510, vol. 53.
Christopher P. Baran et al., "Important Roles for Macrophage Colony-stimulating Factor, CC Chemokine Ligand 2, and Mononuclear Phagocytes in the Pathogenesis of Pulmonary Fibrosis", American Journal of Respiratory and Critical Care Medicine, 2007, pp. 78-89, vol. 176.
Jun-Ichi Ashitani et al., "Granulocyte-colony stimulating factor levels in bronchoalveolar lavage fluid from patients with idiopathic pulmonary fibrosis", Thorax, 1999, pp. 1015-1020, vol. 54.
Kenji Adachi, et al., "Effects of Granulocyte Colony-Stimulating Factor (G-CSF) on Bleomycin-Induced Lung Injury of Varying Severity", Toxicologic Pathology, 2003, pp. 665-673, vol. 31.
Korean Office Action for corresponding KR 10-2020-0010727, Jun. 16, 2021.
International Search Report for PCT/KR2020/001404, dated May 26, 2020.
Communication dated May 31, 2024, issued in Chinese Application No. 202080012031.2.

* cited by examiner

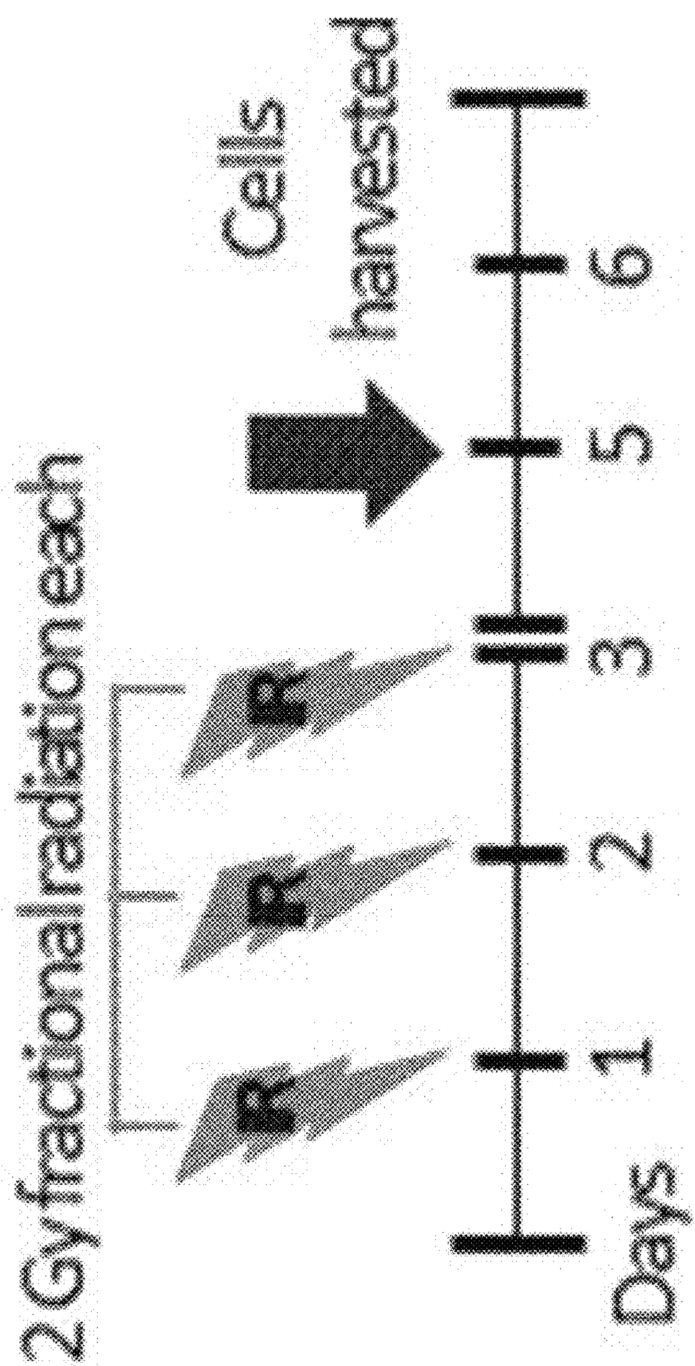
[Fig. 1]

[Fig. 2]
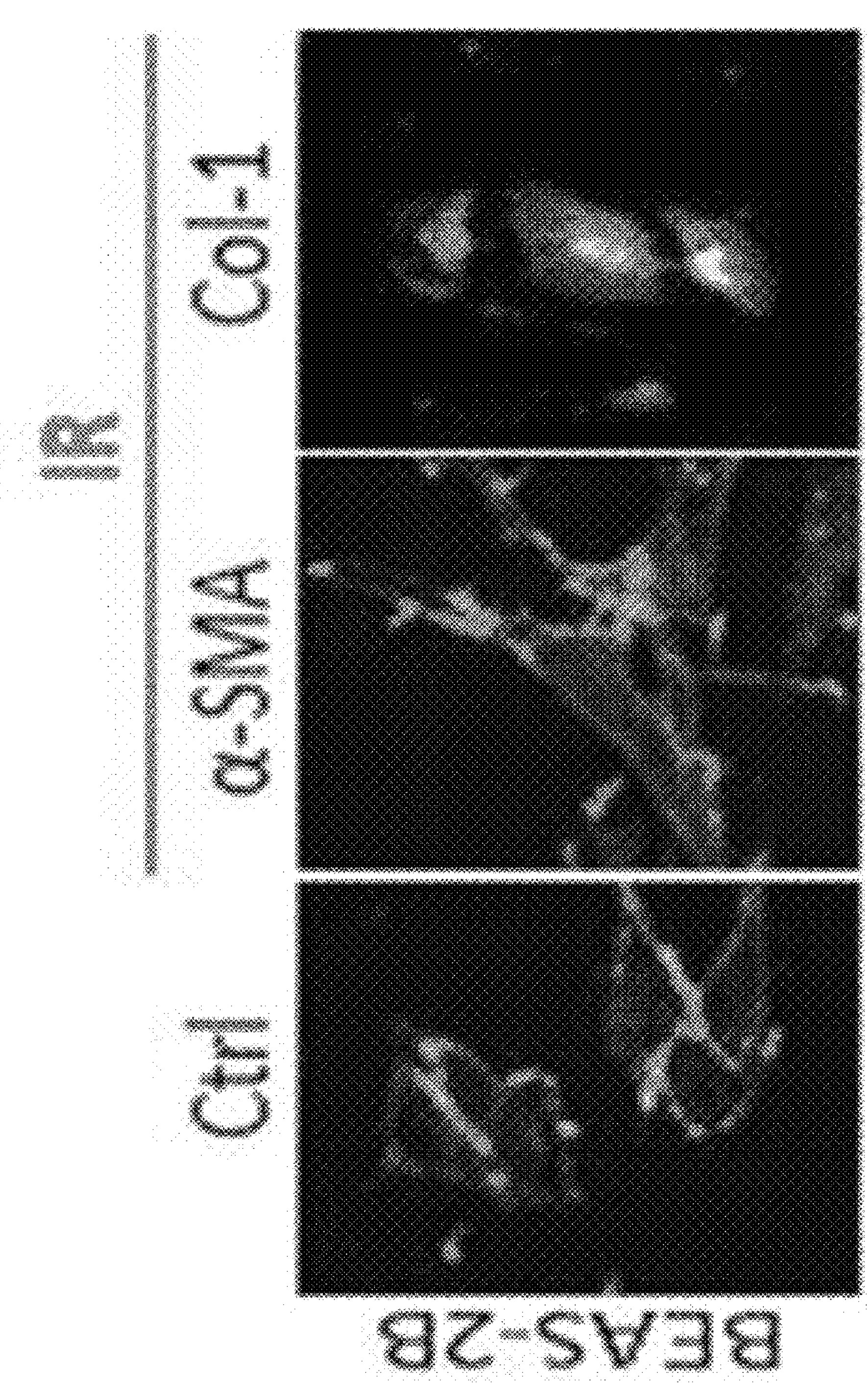

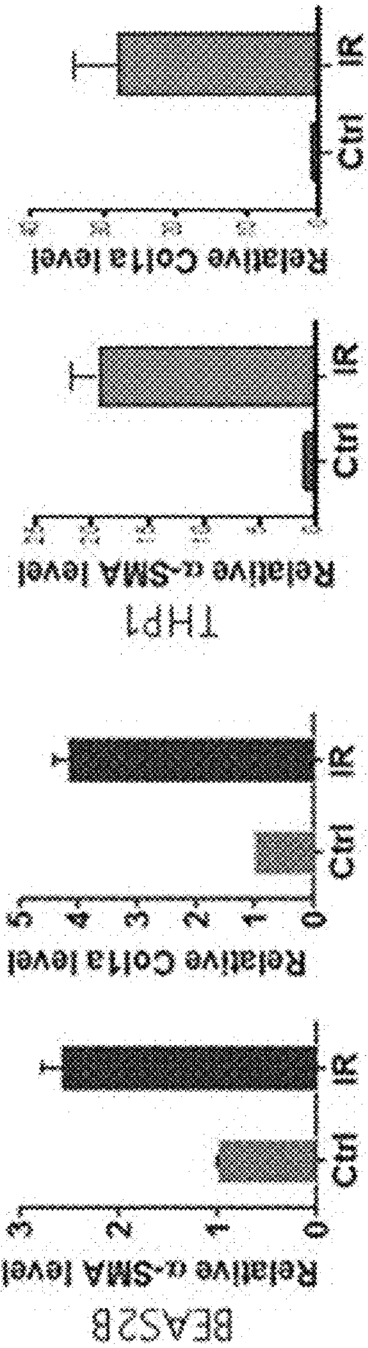
[Fig. 3]

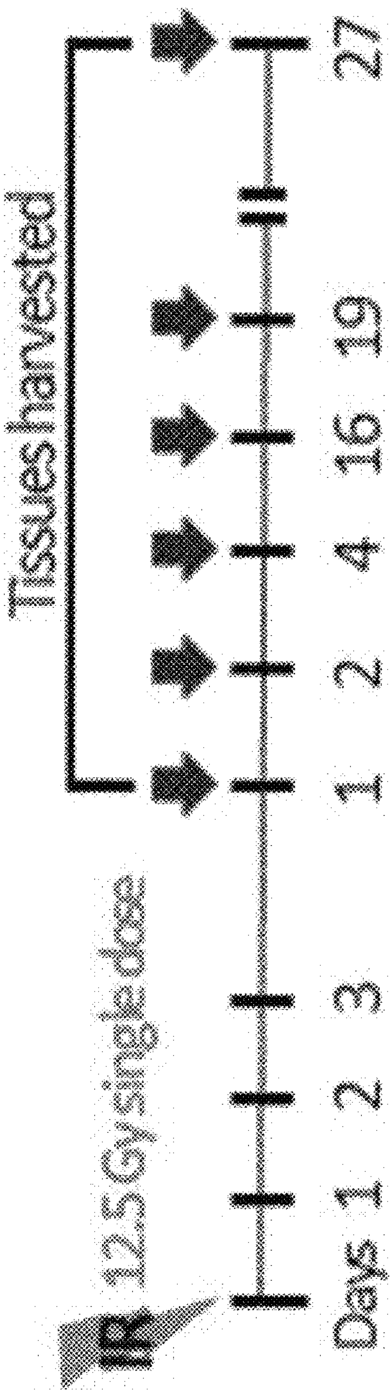
[Fig. 4]

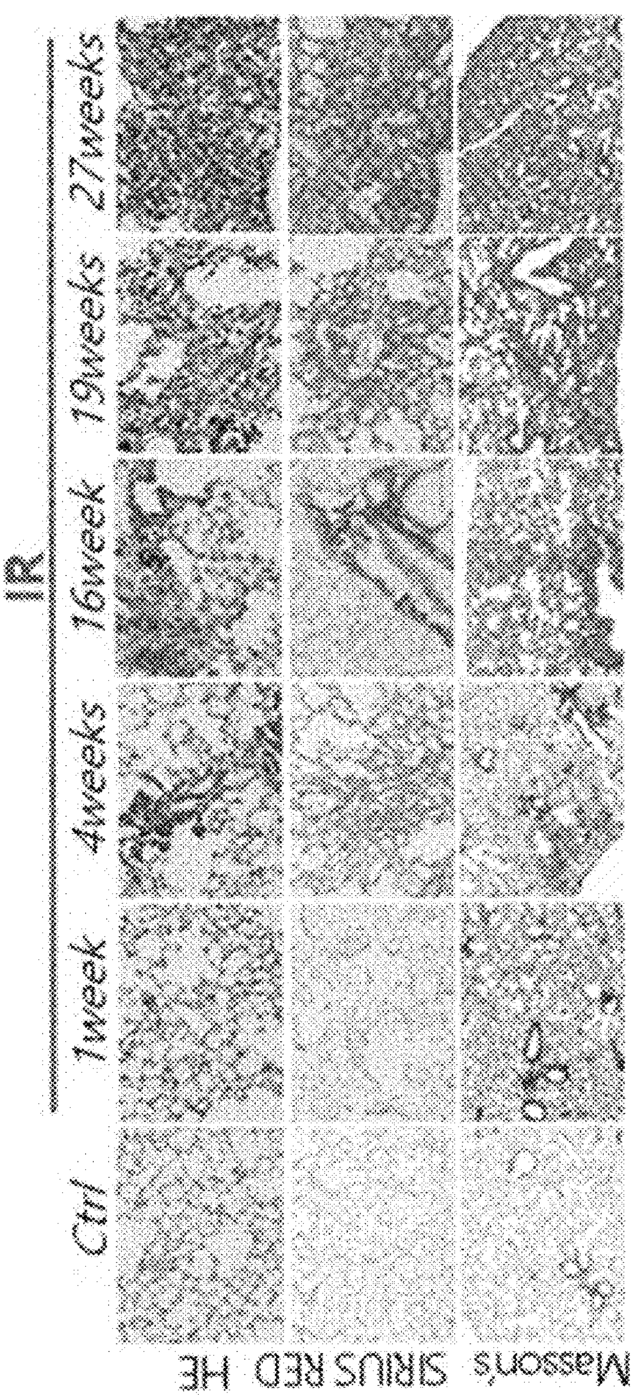
[Fig. 5]

[Fig. 6]
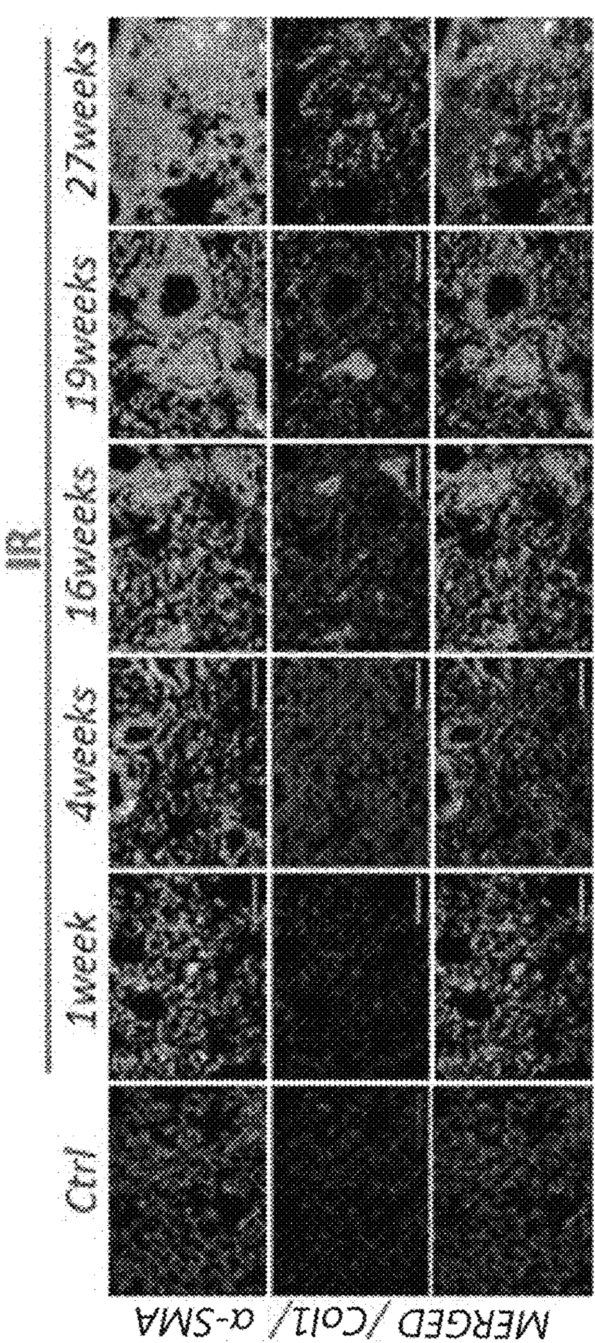

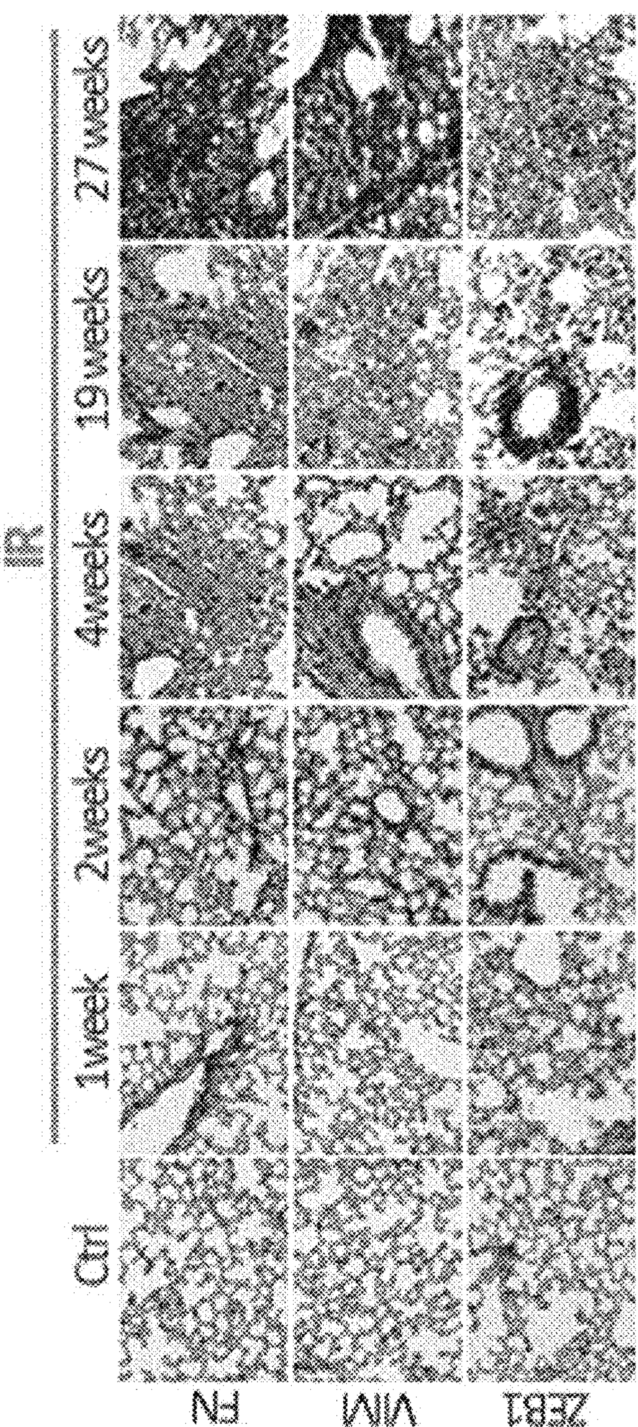
[Fig. 7]

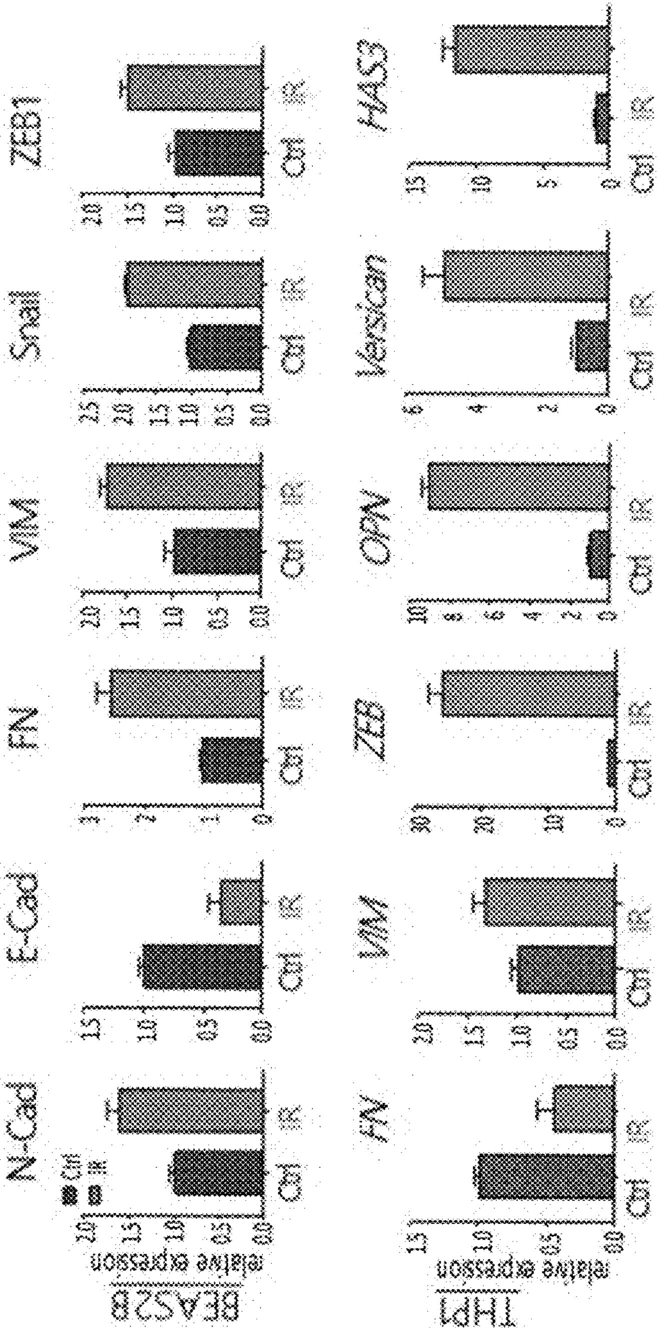
[Fig. 8]

【Fig 9】
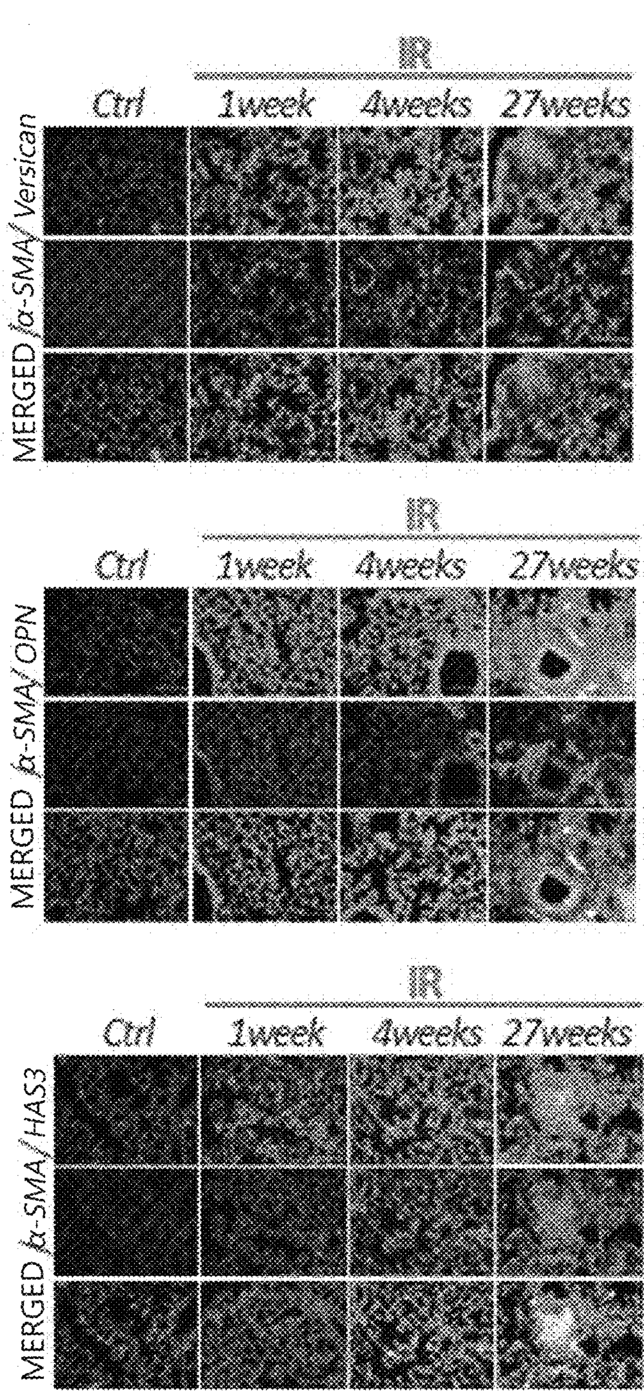

[Fig. 10]
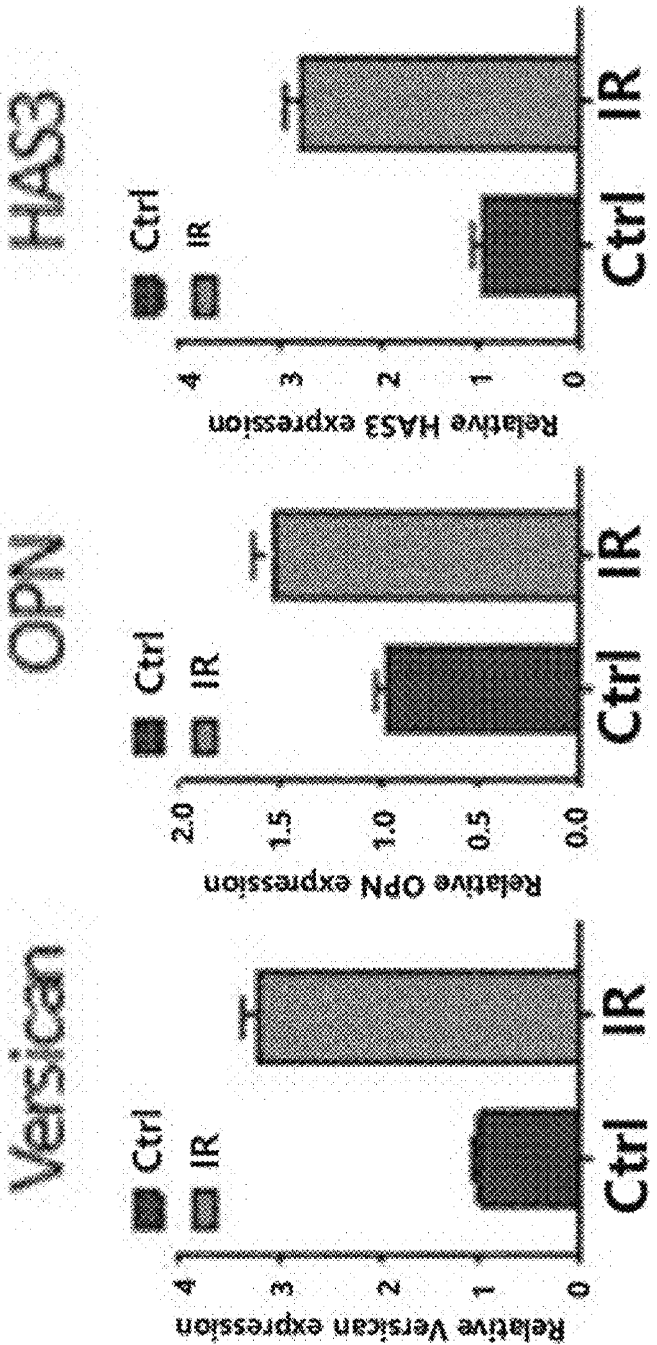

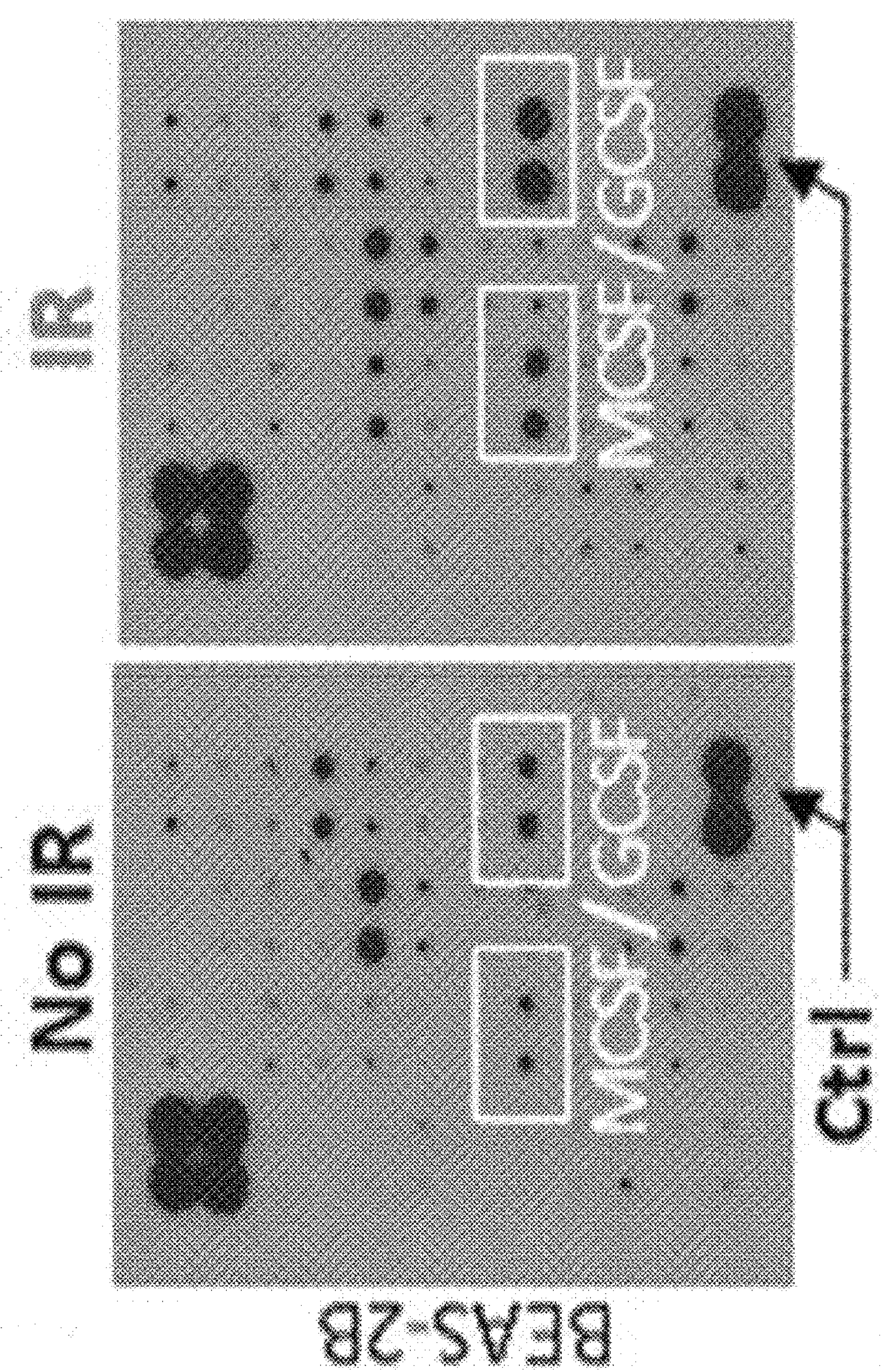
[Fig. 11]

[Fig. 12]
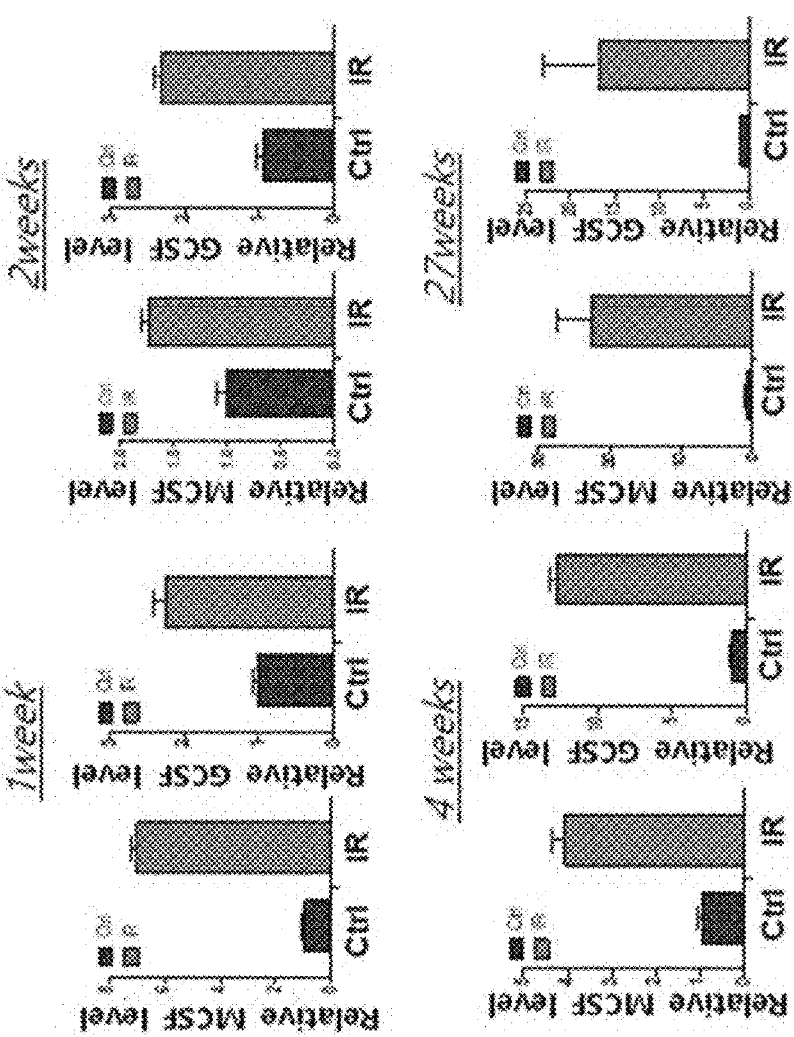

[Fig. 13]
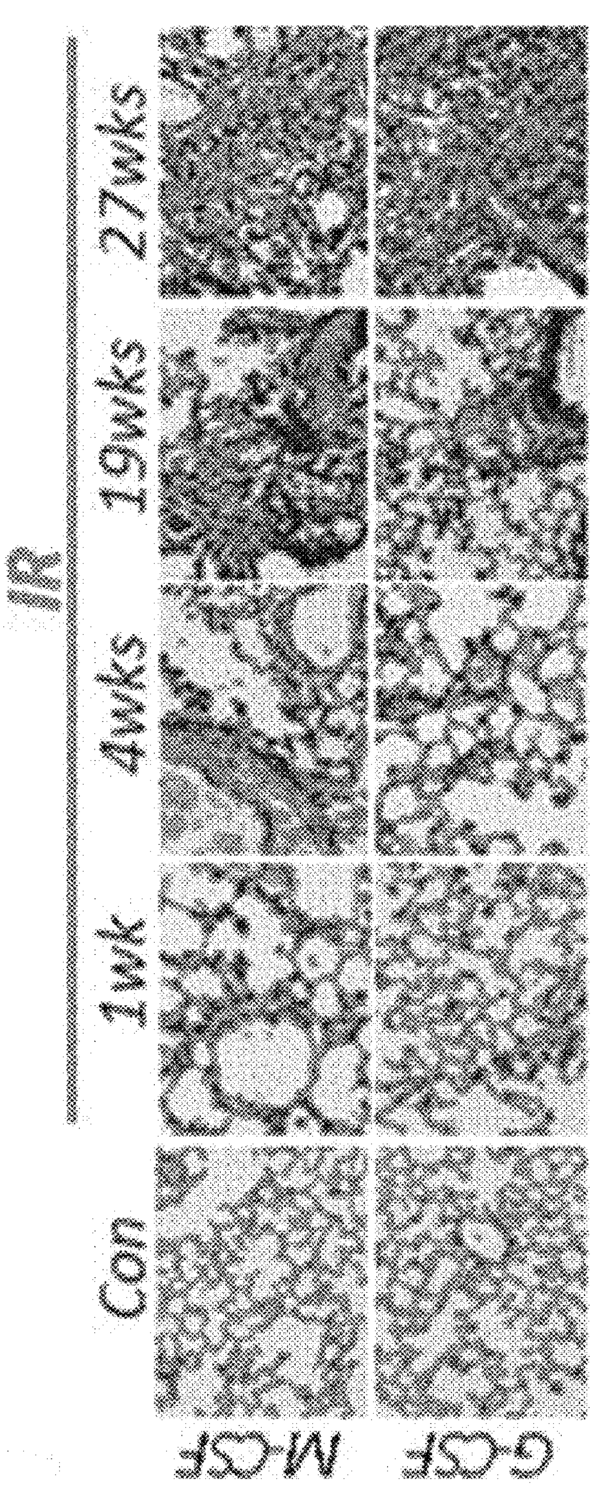

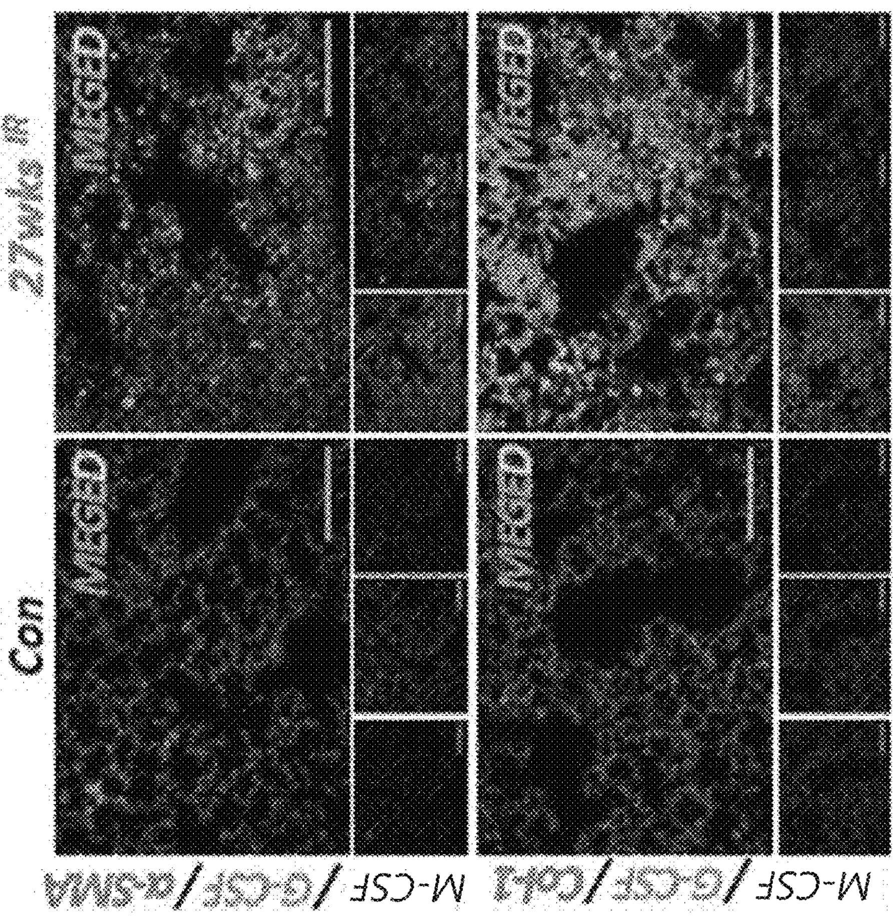
[Fig. 14]

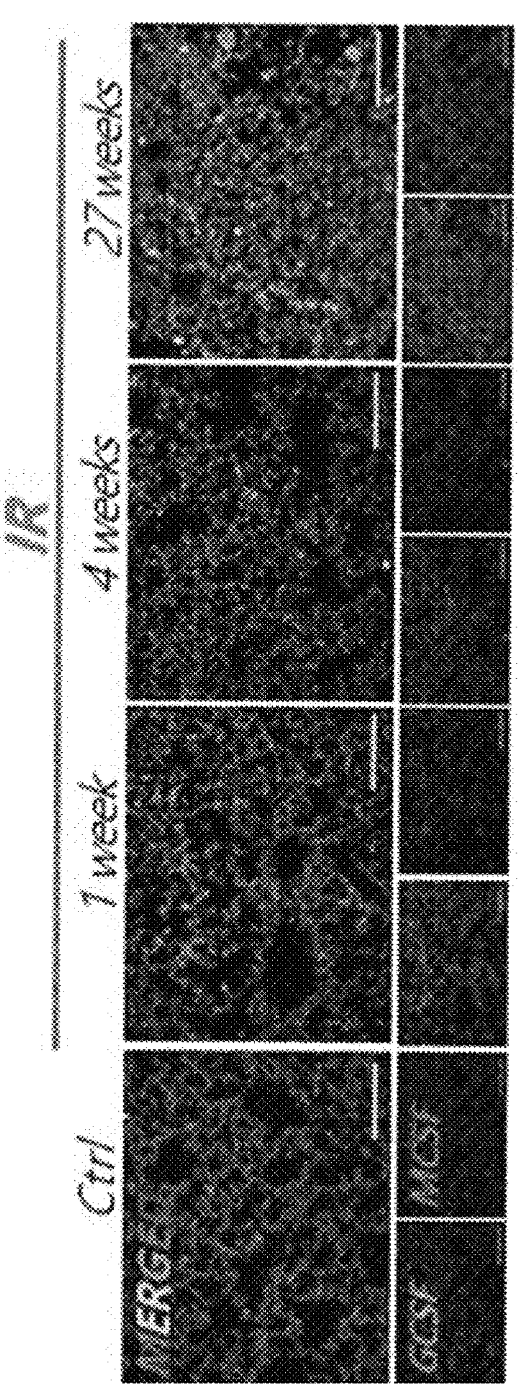
[Fig. 15]

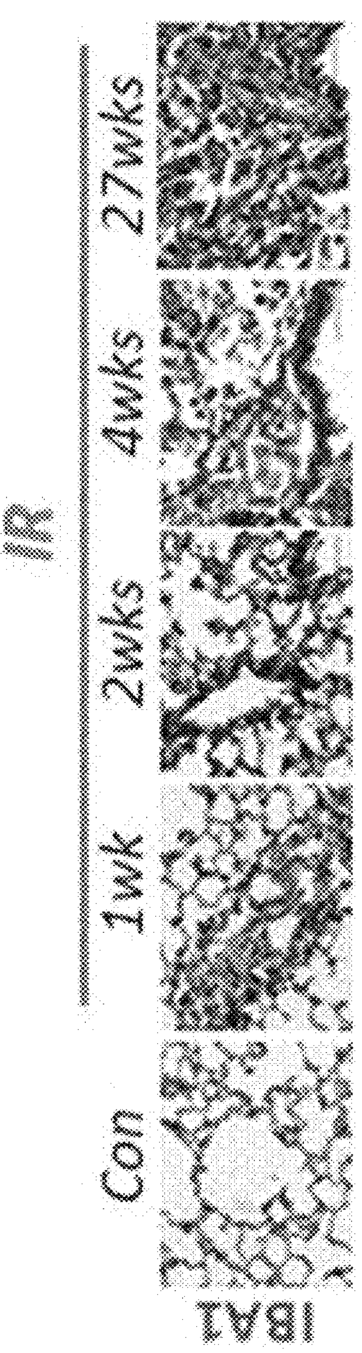
[Fig. 16]

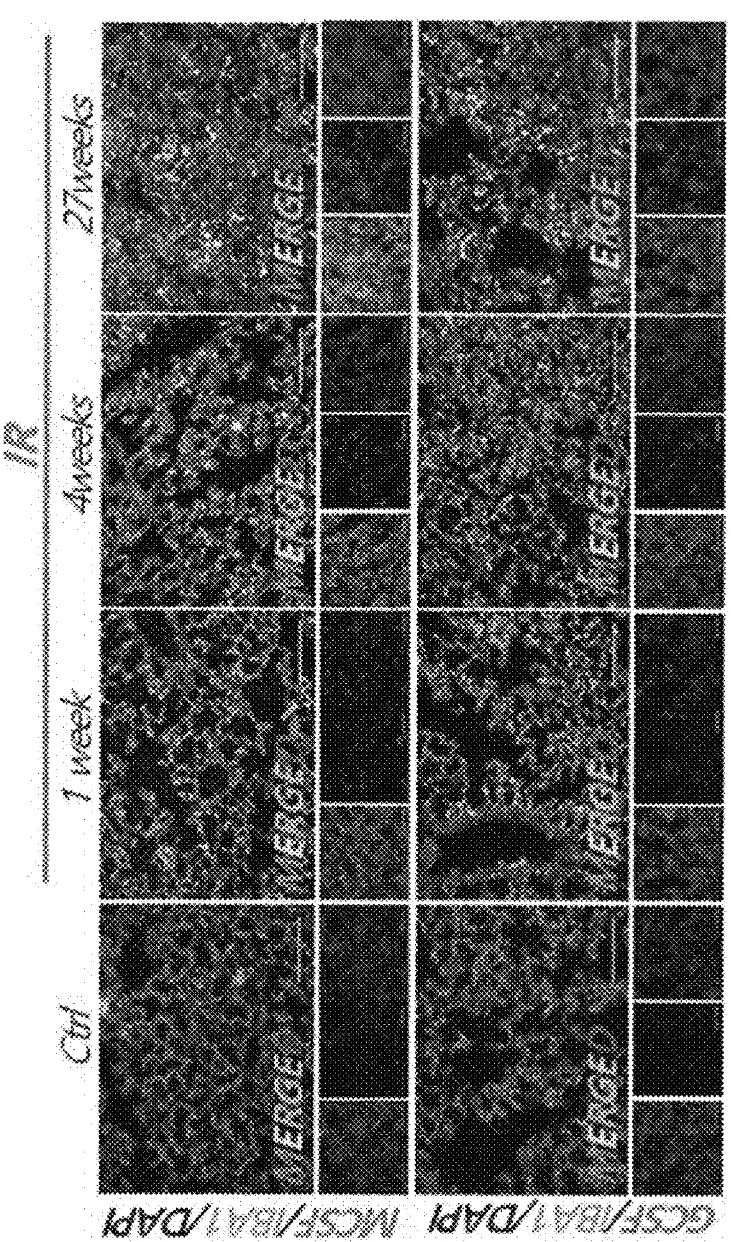
[Fig. 17]

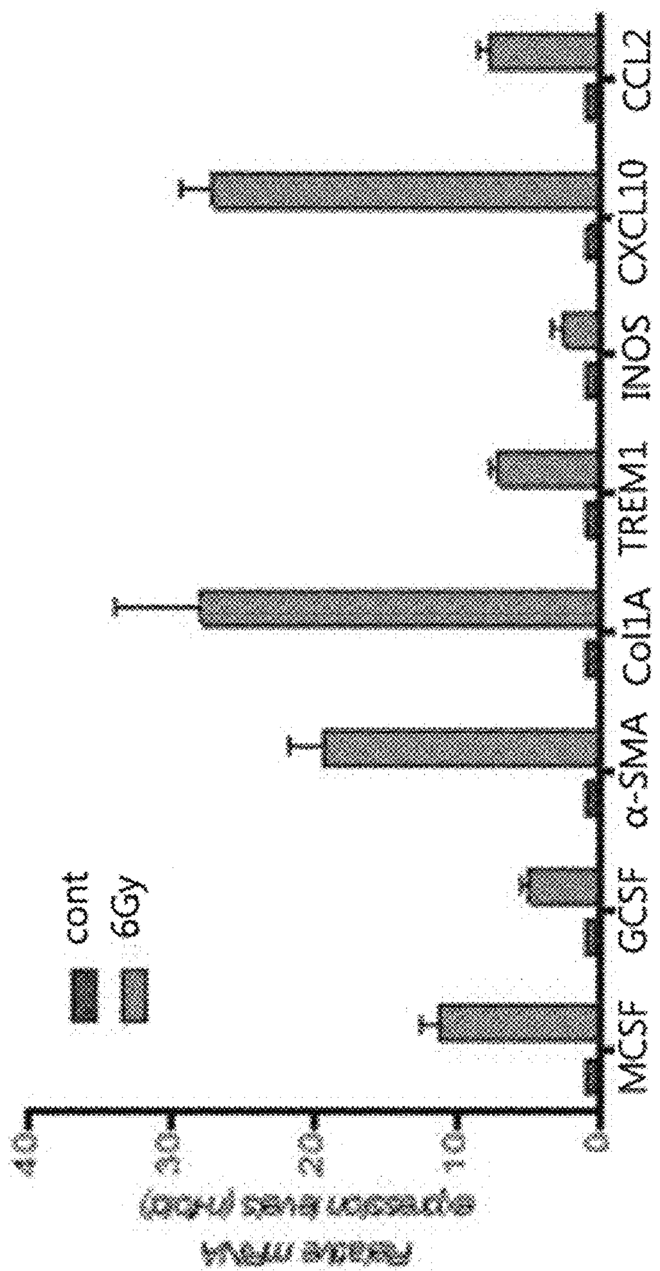
[Fig. 18]

[Fig. 19]
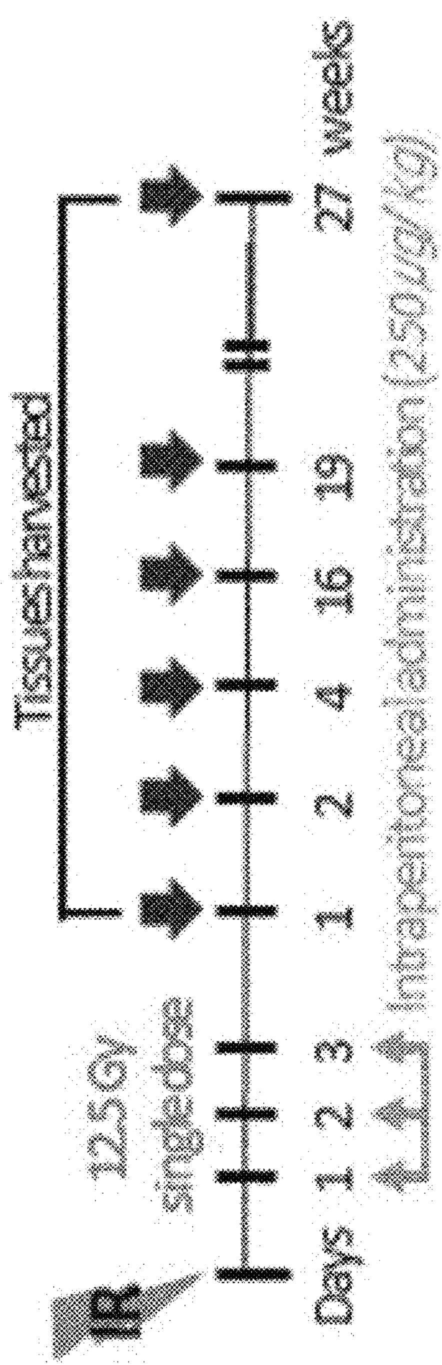

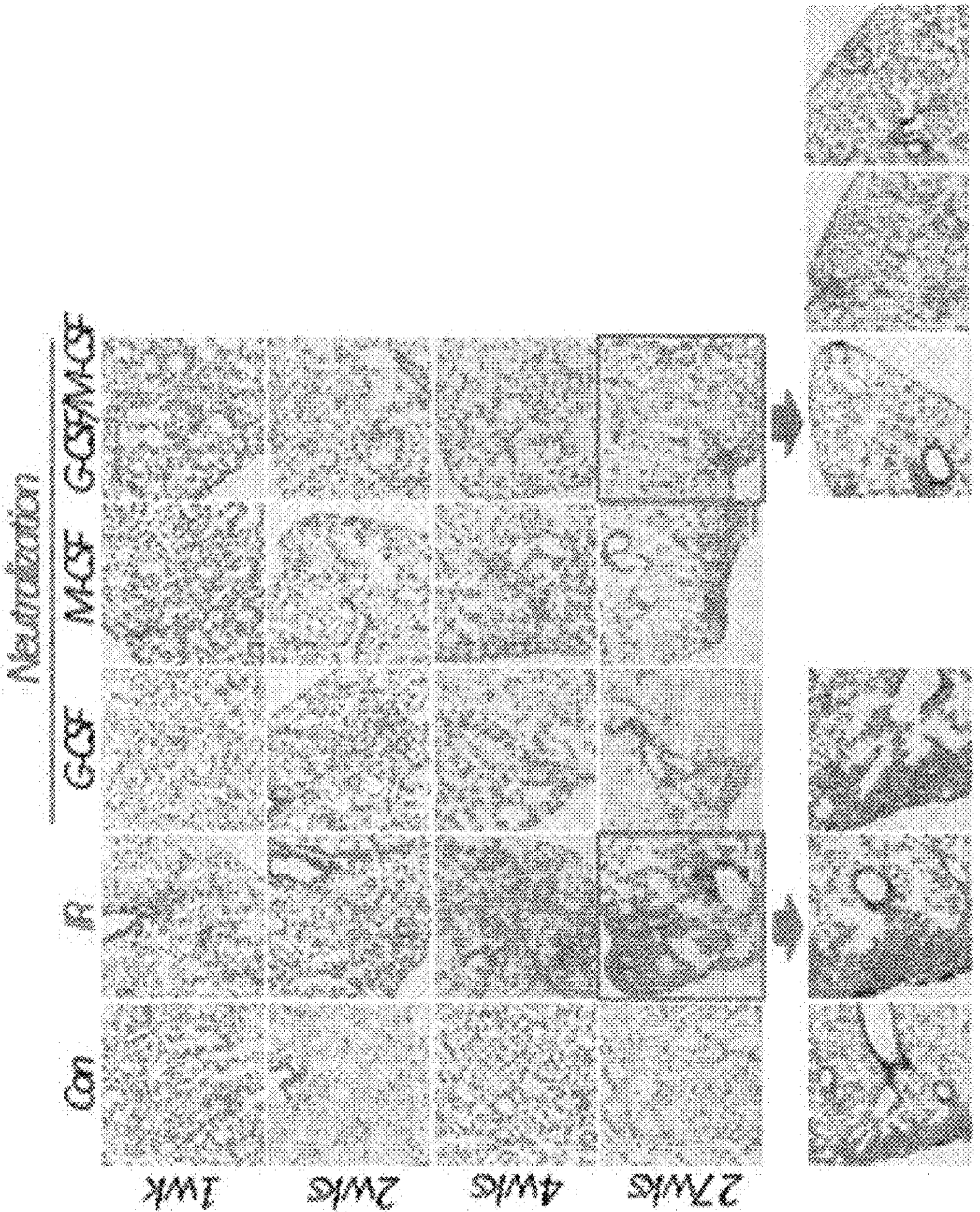
[Fig. 20]

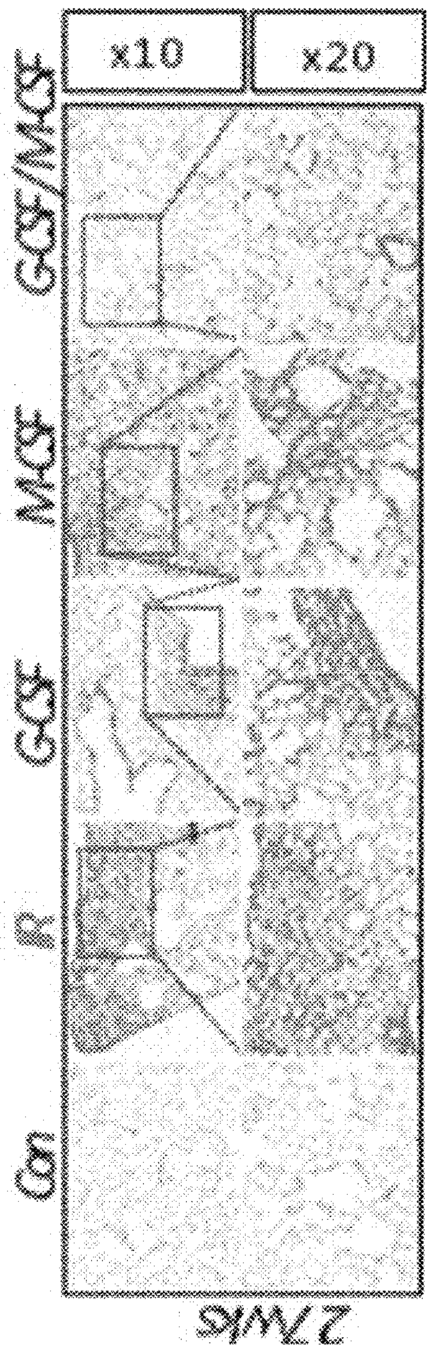
[Fig. 21]

[Fig. 22]
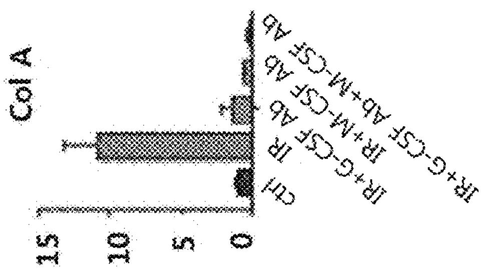
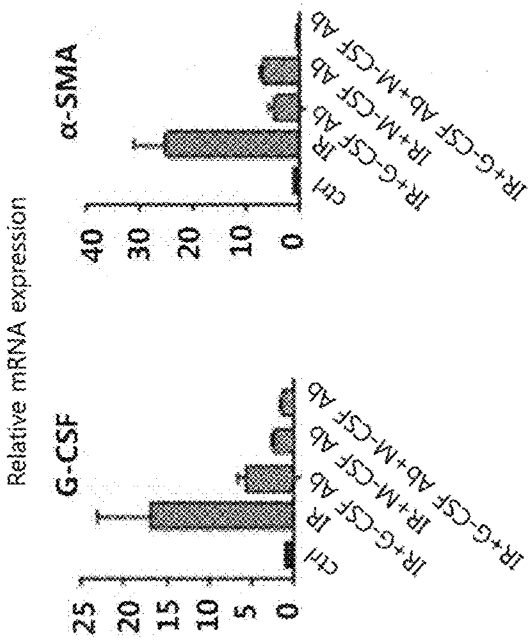
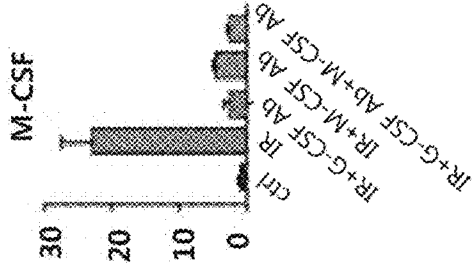

【Fig 23】
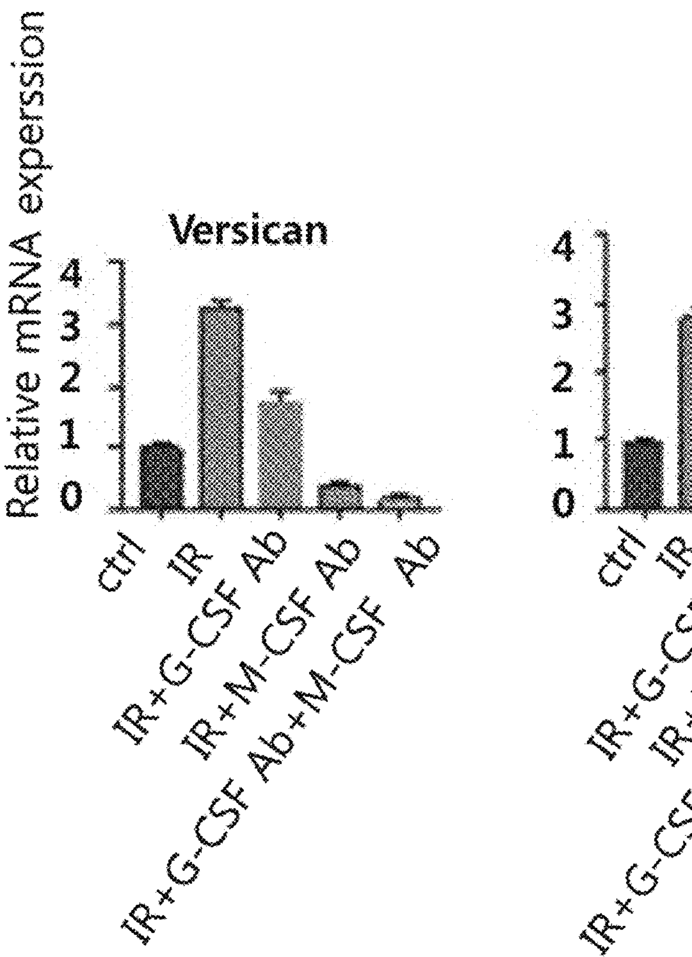

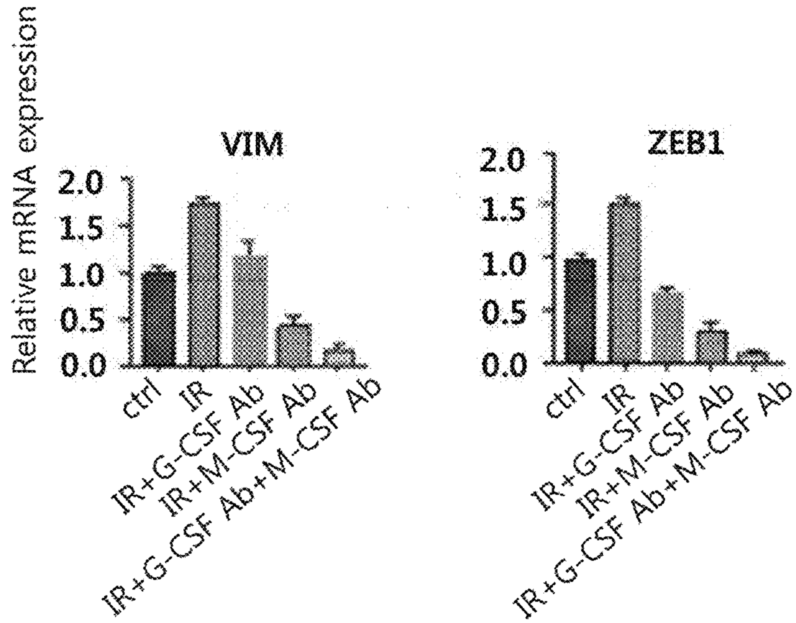
【Fig 24】

[Fig. 25]
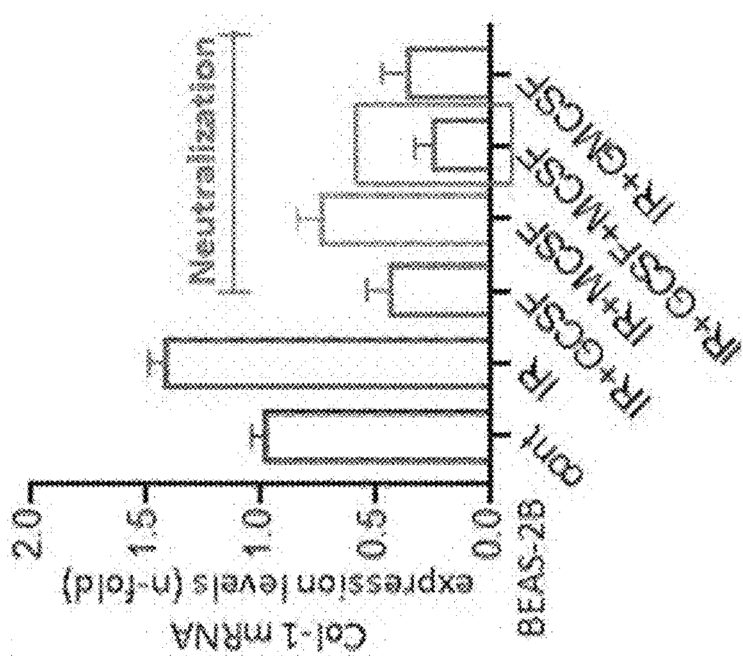
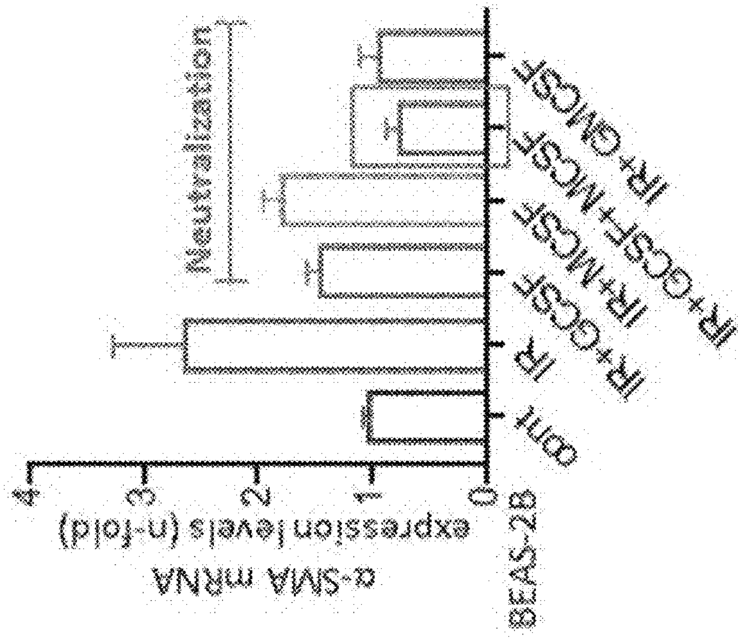

[Fig. 26]
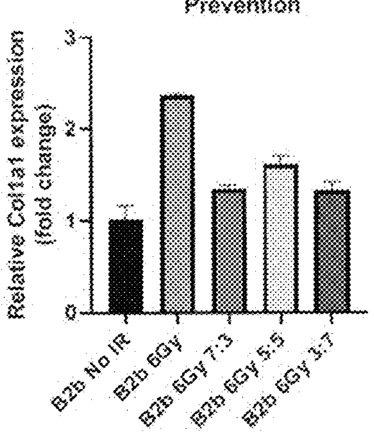
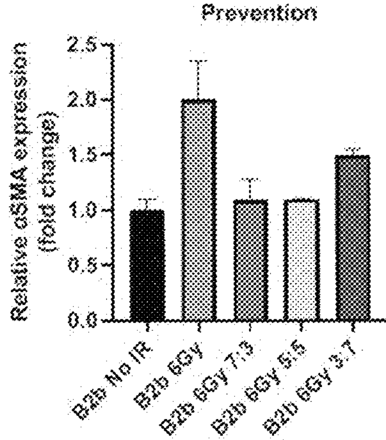
Beas2B each $3x10^5$ Setting
Radiation 6Gy => Immediately antibody treat => 48h after harvest
B2b No IR = Beas2b No IR(control)
B2b 6Gy = Beas2b 6Gy
B2b 6Gy 7:3 = Beas2b 6Gy G-CSF : M-CSF = 7 : 3
B2b 6Gy 7:3 = Beas2b 6Gy G-CSF : M-CSF = 5 : 5
B2b 6Gy 7:3 = Beas2b 6Gy G-CSF : M-CSF = 3 : 7

[Fig. 27]
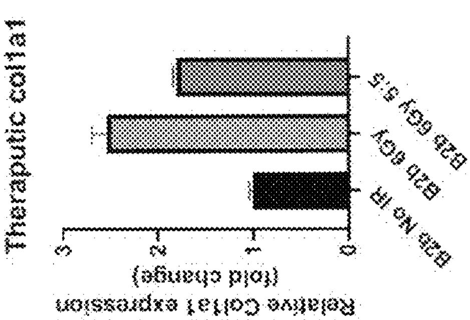
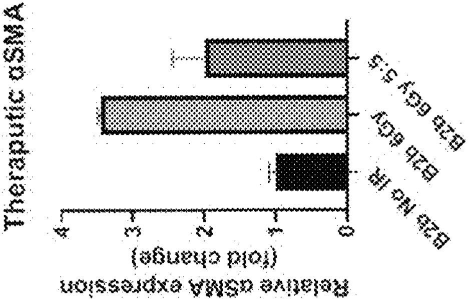
Beas2B each 2X10[5] Setting
Radiation 6Gy => 24h after antibody treat => 48h after harvest
B2b No IR = Beas2b No IR(control)
B2b 6Gy = Beas2b 6Gy
B2b 6Gy 7:3 = Beas2b 6Gy G-CSF : M-CSF = 5 : 5

USE OF M-CSF OR G-CSF FOR DIAGNOSIS OR TREATMENT OF PULMONARY FIBROSIS

CROSS REFERENCE TO RELATED APPLICATIONS

This application is a National Stage of International Application No. PCT/KR2020/001404 filed Jan. 30, 2020, claiming priority based on Korean Patent Application No. 10-2019-0011843 filed Jan. 30, 2019 and Korean Patent Application No. 10-2020-0010727 filed Jan. 29, 2020.

REFERENCE TO SEQUENCE LISTING

The content of the electronically submitted sequence listing, file name: Sequence_Listing_As_Filed.txt; size: 8.60 KB; and date of creation: Feb. 14, 2022, filed herewith, is incorporated herein by reference in its entirety.

TECHNICAL FIELD

The present disclosure describes a use of M-CSF or G-CSF for diagnosis or treatment of pulmonary fibrosis and, more specifically, to: a marker for diagnosing the level of development or progression of pulmonary fibrosis, comprising M-CSF and/or G-CSF; and a composition for preventing or treating pulmonary fibrosis, comprising an M-CSF inhibitor and a G-CSF inhibitor as active ingredients.

BACKGROUND ART

When damage occurs, most organs experience various inflammatory and healing responses. When the degree of damage is negligible, the damage is healed while maintaining normal structures and functions, but in the case of continuous damage or severe damage, the original function of a tissue is lost during the healing process, various factors are accumulated around a damaged site, and tissue fibrosis occurs. During the fibrosis process as described above, the main components of the extracellular matrix (ECM) such as collagen, fibronectin, and elastin are accumulated together in a tissue to form an abnormal structure and generate dysfunction. In particular, radiation used in the treatment of lung cancer and breast cancer is known as a fatal factor which induces damage to heart or lung tissue to provide the possibility of pulmonary fibrosis. In particular, since the heart and lungs are the main organs which represent the circulatory system, problems which are directly related to the patient's life and quality of life may be caused even though the possibility of inducing fibrosis is low, and accordingly, the development of effective treatments and therapeutic agents for fibrotic diseases is indispensable.

Meanwhile, as a granulocyte-colony stimulating factor, G-CSF is a leukocyte activator which kills viruses, molds, bacteria, and the like which invade the body. Recently, G-CSF has been developed as a therapeutic agent for neutropenia, and as a result, the number of cases where G-CSF is applied to cancer patients tends to be increasing, and G-CSF is used as a drug which stimulates granulocyte production in combination with antibiotics or antifungal agents for patients with decreased bone marrow function after anti-cancer drugs and radiation therapy. Further, as a macrophage-colony stimulating factor, M-CSF is an important hematopoietic factor which acts on bone marrow progenitor cells to induce proliferation and then differentiation into granule cells and macrophages.

Studies on TGF-β and IFN-γ, which are commonly expressed in fibrotic diseases of various organs, have been reported, but the materials cannot guarantee the sustainability of a therapeutic effect due to the influence of various signals in the human body, and although there are studies on therapeutic agents for chronic obstructive pulmonary disease associated with fibroblast growth factor-2 (Korean Patent No. 10-0785969), studies on a biomarker use of M-CSF or G-CSF or a therapeutic agent for pulmonary fibrosis using a mixed antibody targeting M-CSF and G-CSF have been insufficient.

DISCLOSURE

Technical Problem

The present disclosure has been devised to solve the aforementioned problems, and as a result of performing various studies to discover a marker capable of predicting diseases associated with fibrosis of pulmonary cells, which are side effects which may occur during radiation therapy for lung cancer cells and an effective material capable of suppressing the diseases, the present inventors have ascertained that a marker containing M-CSF and/or G-CSF can be used for diagnosing pulmonary fibrotic diseases, and that the onset of myofibroblast hyperplasia or pulmonary fibrosis of pulmonary cells can be significantly suppressed using a mixed composition of an anti-M-CSF antibody and an anti-G-CSF antibody to suppress M-CSF and G-CSF, thereby completing the present disclosure based on this.

Thus, an object of the present disclosure is to provide a composition for preventing or treating pulmonary fibrosis, comprising a macrophage-colony stimulating factor (M-CSF) inhibitor and a granulocyte-colony stimulating factor (G-CSF) inhibitor as active ingredients.

Another object of the present disclosure is to provide a marker composition for diagnosing pulmonary fibrosis or for diagnosing the progression of pulmonary fibrosis, comprising one or more selected from the group consisting of a macrophage-colony stimulating factor (M-CSF) and a granulocyte-colony stimulating factor (G-CSF).

Still another object of the present disclosure is to provide a composition for diagnosing pulmonary fibrosis or for diagnosing the progression of pulmonary fibrosis, comprising a preparation which measures the level of mRNA of one or more genes selected from the group consisting of a macrophage-colony stimulating factor (M-CSF) and a granulocyte-colony stimulating factor (G-CSF) or a protein which the gene encodes.

Yet another object of the present disclosure is to provide a kit for diagnosing pulmonary fibrosis or for diagnosing the progression of pulmonary fibrosis, comprising the composition.

Yet another object of the present disclosure is to provide an information providing method for diagnosing pulmonary fibrosis or for diagnosing the level of the progression of pulmonary fibrosis, the method comprising the following steps:

(a) measuring the expression level of one or more selected from the group consisting of M-CSF and G-CSF in a sample derived from a subject; and (b) when the expression level is increased compared to that of a normal control as a result of measuring the expression level of one or more selected from the group consisting of M-CSF and G-CSF, determining pulmonary fibrosis or determining that pulmonary fibrosis is progressing.

Yet another object of the present disclosure is to provide a method for screening a therapeutic agent for pulmonary fibrosis, comprising the following steps:

(1) treating pulmonary epithelial cells derived from a subject with a candidate material;

(2) measuring the expression level of one or more selected from the group consisting of M-CSF and G-CSF in the cells; and (3) selecting a material which reduces the expression level of one or more selected from the group consisting of M-CSF and G-CSF compared to a group not treated with the candidate material as a therapeutic material.

However, technical problems to be solved by the present disclosure are not limited to the aforementioned problems, and other problems that are not mentioned may be clearly understood by the person skilled in the art from the following description.

Technical Solution

To achieve the above objects, the present disclosure provides a composition for preventing or treating pulmonary fibrosis, comprising a macrophage-colony stimulating factor (M-CSF) inhibitor and a granulocyte-colony stimulating factor (G-CSF) inhibitor as active ingredients.

As an exemplary embodiment of the present disclosure, the pulmonary fibrosis may be induced by irradiation.

As another exemplary embodiment of the present disclosure, the pulmonary fibrosis may include myofibroblast hyperplasia or pulmonary fibrosis of pulmonary cells.

As still another exemplary embodiment of the present disclosure, the M-CSF inhibitor may be an anti-M-CSF antibody, and the G-CSF inhibitor may be an anti-G-CSF antibody.

As yet another exemplary embodiment of the present disclosure, the composition may inhibit the differentiation of pulmonary cells into myofibroblasts.

As yet another exemplary embodiment of the present disclosure, the composition may inhibit the epithelial to mesenchymal transition (MT).

As yet another exemplary embodiment of the present disclosure, the composition may inhibit extracellular matrix remodeling (ECM remodeling).

As yet another exemplary embodiment of the present disclosure, the inhibition of differentiation into myofibroblasts inhibits the expression of α-smooth muscle actin (α-SMA).

As yet another exemplary embodiment of the present disclosure, the inhibition of the epithelial to mesenchymal transition may inhibit the expression of one or more proteins selected from the group consisting of fibronectin (FN), vimentin (VIM), and ZEB1.

As yet another exemplary embodiment of the present disclosure, the inhibition of extracellular matrix remodeling may inhibit the expression of one or more proteins selected from the group consisting of versican, osteopontin (OPN), collagen, and HAS3.

Further, the present disclosure provides a method for preventing or treating pulmonary fibrosis, the method comprising administering the composition to a subject.

In addition, the present disclosure provides a use of the composition for prevention or treatment of pulmonary fibrosis.

Furthermore, the present disclosure provides a marker composition for diagnosing pulmonary fibrosis or for diagnosing the progression of pulmonary fibrosis, comprising one or more selected from the group consisting of a macrophage-colony stimulating factor (M-CSF) and a granulocyte-colony stimulating factor (G-CSF).

As an exemplary embodiment of the present disclosure, the pulmonary fibrosis may be induced by irradiation.

As another exemplary embodiment of the present disclosure, the pulmonary fibrosis may include myofibroblast hyperplasia or pulmonary fibrosis of pulmonary cells.

Further, the present disclosure provides a composition for diagnosing pulmonary fibrosis or for diagnosing the progression of pulmonary fibrosis, comprising a preparation which measures the level of mRNA of one or more genes selected from the group consisting of a macrophage-colony stimulating factor (M-CSF) and a granulocyte-colony stimulating factor (G-CSF) or a protein which the gene encodes.

Further, the present disclosure provides a kit for diagnosing pulmonary fibrosis or for diagnosing the progression of pulmonary fibrosis, comprising the composition.

In addition, the present disclosure provides an information providing method for diagnosing pulmonary fibrosis or for diagnosing the level of progression of pulmonary fibrosis, the method comprising the following steps:

(a) measuring the expression level of one or more selected from the group consisting of M-CSF and G-CSF in a sample derived from a subject; and (b) when the expression level is increased compared to that of a normal control as a result of measuring the expression level of one or more selected from the group consisting of M-CSF and G-CSF, determining pulmonary fibrosis or determining that pulmonary fibrosis is progressing.

Furthermore, the present disclosure provides a method for screening a therapeutic agent for pulmonary fibrosis, the method comprising the following steps:

(1) treating pulmonary epithelial cells of a subject with a candidate material;

(2) measuring the expression level of one or more selected from the group consisting of M-CSF and G-CSF in the cells; and (3) selecting a material which reduces the expression level of one or more selected from the group consisting of M-CSF and G-CSF compared to a group not treated with the candidate material as a therapeutic material.

Advantageous Effects

The present inventors have ascertained that M-CSF and/or G-CSF is a marker for development or progression of pulmonary fibrosis, and have confirmed that a composition, which comprises M-CSF and G-CSF and which binds to M-CSF and G-CSF so that the inherent mechanism thereof can be prevented, has an effect of significantly inhibiting myofibroblast hyperplasia or pulmonary fibrosis of pulmonary cells, and thus the marker and the composition of the present disclosure are expected to be effectively usable for diagnosis, prevention or treatment of pulmonary fibrosis.

DESCRIPTION OF DRAWINGS

FIG. 1 illustrates an experimental plan for reproducible radiation therapy for a BEAS-2B cell line.

FIG. 2 illustrates the results of confirming whether α-smooth muscle actin (α-SMA) is expressed and collagen is accumulated in radiation-exposed epithelial cells.

FIG. 3 illustrates the results of confirming whether α-smooth muscle actin (α-SMA) is expressed and collagen is accumulated in radiation-exposed epithelial cells by measuring the mRNA expression level.

FIG. 4 illustrates an experimental plan for irradiation of an experimental animal model with radiation.

FIG. 5 illustrates the results of confirming changes in pulmonary tissue over time after local irradiation with radiation in an experimental animal model by HE staining, SIRIUS RED staining, and Masson's trichrome staining.

FIG. 6 illustrates the results of confirming the proliferation of myofibroblasts and the secretion of collagen over time after local irradiation with radiation in an experimental animal model.

FIG. 7 illustrates the results of confirming whether markers and regulators for the epithelial to mesenchymal transition are expressed in a pulmonary parenchymal tissue of an experimental animal model with induced pulmonary fibrosis.

FIG. 8 illustrates the results of confirming whether markers and regulators for the epithelial to mesenchymal transition are expressed in a pulmonary parenchymal tissue of an experimental animal model with induced pulmonary fibrosis by measuring the mRNA expression level.

FIG. 9 illustrates the results of confirming progression of extracellular matrix remodeling by observing the expression pattern of extracellular matrix constituents in pulmonary fibrotic tissue.

FIG. 10 illustrates the results of confirming whether an increase in the expression level of extracellular matrix constituents by measuring the mRNA expression level.

FIG. 11 illustrates the results of screening for inflammatory active factors expressed in a pulmonary parenchymal tissue in which damage is induced by radiation.

FIG. 12 illustrates the results of confirming whether the expression of M-CSF and G-CSF is increased by measuring the mRNA expression level in a pulmonary parenchymal tissue in which damage is induced by radiation.

FIG. 13 illustrates the results of confirming whether the expression of M-CSF and G-CSF is increased according to the exacerbation of pulmonary fibrosis injury.

FIG. 14 illustrates the results of confirming whether the expression of M-CSF, G-CSF, α-smooth muscle actin (α-SMA), and collagen is increased according to the exacerbation of pulmonary fibrosis injury.

FIG. 15 illustrates the results of confirming whether the expression of M-CSF and G-CSF is increased according to the exacerbation of pulmonary fibrosis injury.

FIG. 16 illustrates the results of confirming macrophage recruitment mediated by M-CSF and G-CSF for a pulmonary parenchymal tissue.

FIG. 17 illustrates the results of confirming whether the aggregation of macrophages increases as the expression of M-CSF and G-CSF is increased in a pulmonary parenchymal tissue.

FIG. 18 illustrates the results of confirming whether an immune cell activity assessment factor (TRM1), anti-inflammatory macrophage secretory factors (iNOS, CXCL10), and a non-immunized macrophage secretory factor (CCL2) are increased by measuring the mRNA expression level of the above factors.

FIG. 19 illustrates an experimental plan for irradiation with radiation and antibody injection.

FIG. 20 illustrates the results of comparing the pathological changes in a pulmonary parenchymal tissue due to irradiation with the pathological changes in a pulmonary parenchymal tissue injected with a target antibody.

FIG. 21 illustrates the results of comparing the degree of accumulation of extracellular matrix elements in a pulmonary parenchymal tissue of a group irradiated with radiation with the degree of accumulation of extracellular matrix elements in a pulmonary parenchymal tissue of a group injected with a target antibody by collagen staining 27 weeks after irradiation with radiation.

FIG. 22 illustrates the results of comparing the amount of active secretory factor in a group irradiated with radiation (pulmonary parenchymal tissue) with the amount of active secretory factor in a group injected with a target antibody (pulmonary parenchymal tissue).

FIG. 23 illustrates the results of comparing the amount of a regulator of the epithelial to mesenchymal transition in a group irradiated with radiation (pulmonary parenchymal tissue) with the amount of a regulator of the epithelial to mesenchymal transition in a group injected with a target antibody (pulmonary parenchymal tissue).

FIG. 24 illustrates the results of comparing the amount of extracellular matrix constituent in a group irradiated with radiation (pulmonary parenchymal tissue) with the amount of extracellular matrix constituent in a group injected with a target antibody (pulmonary parenchymal tissue).

FIG. 25 illustrates the results of confirming whether the expression of α-smooth muscle actin (α-SMA) and collagen decreases in a group (BEAS-2B) injected with a single target antibody of G-CSF, M-CSF, and GM-CSF and a mixed target antibody of G-CSF/M-CSF by measuring the mRNA expression level.

FIG. 26 illustrates the results of confirming the effects of a mixed target antibody of G-CSF/M-CS on the prevention of a fibrosis disease by measuring the mRNA expression of α-smooth muscle actin (α-SMA) and collagen in a group (BEAS-2B) injected with the mixed target antibody.

FIG. 27 illustrates the results of confirming the effects of a mixed target antibody of G-CSF/M-CS on the treatment of a fibrosis disease by measuring the mRNA expression of α-smooth muscle actin (α-SMA) and collagen in a group (BEAS-2B) injected with the mixed target antibody.

MODES OF THE INVENTION

Hereinafter, the present disclosure will be described in detail.

As a result of observing that the expression of M-CSF and/or G-CSF is increased when fibrosis of normal pulmonary cells occurs during radiation therapy for lung cancer cells and conducting various studies in order to discover a material that inhibits fibrosis of normal pulmonary cells and is effective against lung cancer cells, the present inventors have ascertained that it is possible to significantly inhibit myofibroblast hyperplasia or pulmonary fibrosis of pulmonary cells using M-CSF and/or G-CSF as a marker for determining the development or progression of pulmonary fibrosis, and using a mixed composition of an anti-M-CSF antibody and an anti-G-CSF antibody to inhibit M-CSF and G-CSF, thereby completing the present disclosure.

Thus, the present disclosure provides a marker composition for diagnosing pulmonary fibrosis or for diagnosing the progression of pulmonary fibrosis, comprising one or more selected from the group consisting of a macrophage-colony stimulating factor (M-CSF) and a granulocyte-colony stimulating factor (G-CSF), a composition for diagnosing pulmonary fibrosis or for diagnosing the progression of pulmonary fibrosis, comprising a preparation which measures the level of mRNA of one or more genes selected from the group consisting of the M-CSF and the G-CSF or a protein which the gene encodes, and a kit for diagnosing pulmonary fibrosis or for diagnosing the progression of pulmonary fibrosis, comprising the composition.

The "pulmonary fibrosis", which is a disease targeted by the present disclosure, is a respiratory disease in which lung tissue solidifies to cause a serious respiratory disorder, lung solidification means excessive accumulation of fibrous connective tissue, and this process is referred to as fibrosis. As fibrosis progresses, the lung wall thickens to decrease the amount of oxygen supplied to the blood, resulting in persistent shortness of breath in a patient, and it has been reported that there is no method capable of repairing fibrotic lung tissue. Pulmonary fibrosis with a known cause may be caused by various causes including occupational causes, environmental causes, genetic causes, exposure to radiation, and the like, but the pulmonary fibrosis according to the present disclosure may be induced by irradiation, and may be myofibroblast hyperplasia or pulmonary fibrosis of pulmonary epithelial cells according to the extent of progression of the pulmonary fibrosis, but is not limited thereto.

It is known that the "myofibroblast" in the present disclosure is a cell which induces pulmonary fibrosis, moves to a site damaged by radiation to synthesize and secrete various extracellular matrices and collagens, thereby inducing pulmonary fibrosis, and the myofibroblast expresses α-smooth muscle actin (α-SMA), calponin, SM22α, and the like.

As used herein, the "myofibroblastization" refers to conversion of normal pulmonary cells into myofibroblasts, and the present inventors have found that when normal pulmonary cells are irradiated, normal pulmonary epithelial cells are converted and induced into myofibroblasts. Through this, pulmonary fibrosis is eventually induced.

The "M-CSF" in the present disclosure is a type of cytokine as one of the family of colony stimulating factors, and is also called a macrophage-colony stimulating factor. In general, M-CSF serves to differentiate myeloid precursors into various cells such as monocytes, macrophages, and dendritic cells. In addition, M-CSF is known to affect not only the migration, proliferation and function of macrophages acting in innate or acquired immunity, but also the survival of the macrophages, and is involved in placental development.

The "G-CSF" in the present disclosure is a type of cytokine as one of the family of colony stimulating factors, and is also called a granulocyte-colony stimulating factor. The G-CSF is produced by endothelial cells, macrophages or other immune cells and stimulates bone marrow progenitor cells to induce differentiation into granulocytes and proliferation of granulocytes. Furthermore, the G-CSF is known to induce the survival, proliferation and differentiation of neutrophil precursors and neutrophils and may affect nerve cells as a neurotrophic factor, and thus is used to treat cerebral ischemic diseases.

As used herein, the term "diagnosis" refers to the determination of an actual condition of the disease of a patient in all aspects in a broad sense. The contents of the determination are the disease entity, the pathogenesis, the severity, the detailed aspect of a disease, the presence and absence of complications, and the like. In the present disclosure, the diagnosis is to determine the presence or absence of the onset of pulmonary fibrosis, the level of progression, and the like.

As another aspect of the present disclosure, the present disclosure provides an information providing method for diagnosing pulmonary fibrosis or for diagnosing the level of progression of pulmonary fibrosis, the method comprising (a) when the expression level is increased compared to that of a normal control as a result of measuring the expression level of one or more selected from the group consisting of M-CSF and G-CSF in a sample derived from a subject, determining pulmonary fibrosis or determining that pulmonary fibrosis is progressing.

As used herein, the term "information providing method for diagnosing pulmonary fibrosis" refers to provision of objective basic information necessary for diagnosing pulmonary fibrosis as a preliminary step for diagnosis or prognosis prediction, and excludes the physician's clinical judgment or findings. The sample derived from the subject is not limited to, but may be, for example, a tissue, a cell, or the like.

Further, the present disclosure provides a method for screening a therapeutic agent for pulmonary fibrosis, the method comprising: (1) treating pulmonary epithelial cells of a subject with a candidate material; (2) measuring the expression level of one or more selected from the group consisting of M-CSF and G-CSF in the cells; and (3) selecting a material which reduces the expression level of one or more selected from the group consisting of M-CSF and G-CSF compared to a group not treated with the candidate material as a therapeutic material.

In the present disclosure, examples of a method for measuring the mRNA expression level include polymerase chain reaction (RT-PCR), competitive RT-PCR, real time RT-PCR, RNase protection assay (RPA), Northern blotting, DNA chips, and the like, but are not limited thereto.

In the present disclosure, examples of a method for measuring the expression level of a protein include enzyme linked immunosorbent assay (ELISA), radioimmunoassay (RIA), an Ouchterlony immunodiffusion method, rocket immunoelectrophoresis, tissue immunostaining, an immunoprecipitation assay, a complement fixation assay, fluorescence activated cell sorter (FACS), a protein chip, and the like, but are not limited thereto.

In addition, the present disclosure provides a composition for preventing or treating pulmonary fibrosis, comprising a macrophage-colony stimulating factor (M-CSF) inhibitor and a granulocyte-colony stimulating factor (G-CSF) inhibitor as active ingredients.

The M-CSF inhibitor according to the present disclosure may be an anti-M-CSF antibody, the G-CSF inhibitor may be an anti-G-CSF antibody, and the antibody according to the present disclosure may inhibit the differentiation of pulmonary cells into myofibroblasts, the epithelial to mesenchymal transition (EMT) or extracellular matrix remodeling (ECM remodeling).

Furthermore, the inhibition of differentiation of pulmonary cells into myofibroblasts according to the present disclosure may inhibit the expression of α-smooth muscle actin (α-SMA). The inhibition of the epithelial to mesenchymal transition according to the present disclosure may inhibit the expression of one or more proteins selected from the group consisting of fibronectin (FN), vimentin (VIM), and ZEB1. The inhibition of extracellular matrix remodeling according to the present disclosure may inhibit the expression of one or more proteins selected from the group consisting of versican, osteopontin (OPN), collagen, and HAS3.

The "epithelial to mesenchymal transition" according to the present disclosure refers to a process in which epithelial cells become mesenchymal stem cells by losing cell polarity and intercellular adhesion and obtaining a mobile phase and invasiveness, and these are pluripotent stromal cells which may differentiate into various cell types. The epithelial to mesenchymal transition is essential for many developmental processes including mesoderm formation and neurulation, and is observed during wound healing, organ fibrosis and cancer metastasis.

The "extracellular matrix remodeling" according to the present disclosure refers to quantitative and qualitative changes in the extracellular matrix in the neoplastic transformation process which promotes tumor growth and metastasis. The extracellular matrix is produced and assembled under the influence of surrounding cells, and the main components of the extracellular matrix are glycosaminoglycans and proteoaminoglycans, noncollagenous glycoproteins such as fibronectin, laminin, or tenascin, collagen, and biomolecules associated with interactions between cells or between cells and a substrate. When the morphology and properties of surrounding cells change due to some factors, the composition or properties of the extracellular matrix also change accordingly.

As described above in the present disclosure, various studies have been conducted to confirm that M-CSF and G-CSF are involved in the development of pulmonary fibrosis by radiation irradiated to treat cancer, and in an exemplary embodiment of the present disclosure, as a result of conducting an experiment which confirms whether the epithelial to mesenchymal transition and extracellular matrix remodeling progress by extracting a pulmonary parenchymal tissue of an experimental animal model with induced fibrosis, it was confirmed that in the pulmonary parenchymal tissue, the expression of markers (fibronectin, vimentin) and a regulator (ZEB1) for the epithelial to mesenchymal transition was greatly increased and the expression of various marker factors (versican, OPN) for extracellular matrix constituents and a main factor (HAS3) for collagen synthesis were increased (see Example 3), and as a result of screening inflammatory active factors for the pulmonary parenchymal tissue, it was confirmed that M-CSF (CSF type 1) and G-CSF (CSF type 3) were detected together with IL-6, IL-8 and TGF-β1, which are commonly secreted from various fibrotic cells. In particular, it was confirmed that the expression of M-CSF and G-CSF was remarkably increased after irradiation with radiation, and that expression of M-CSF and G-CSF was further increased as the pulmonary fibrosis damage was aggravated (see Example 4-1). This confirms that M-CSF or G-CSF has a marker use in diagnosing the development and progression of pulmonary fibrosis.

Further, it was confirmed that the expression of α-smooth muscle actin (α-SMA), which is a marker for myofibroblasts, and collagen, which is a main constituent of the extracellular matrix, were increased with an increase in M-CSF and G-CSF (see Example 4-2).

In another exemplary embodiment of the present disclosure, as a result of intraperitoneally injecting target antibodies of M-CSF (single), G-CSF (single), and MCSF/GCSF (mixed) for 3 hours after 24 hours of exposing the chest of an experimental animal model to radiation, it was confirmed that fibroblastic foci were greatly increased in sites around the lungs and normal sites of a group exposed to radiation and not injected with a target antibody, and although irreparable structural damage to the lungs occurred, a group injected with a single or mixed target antibody of G-CSF and M-CSF greatly reduced the degree of lung damage caused by radiation, and in particular, it was confirmed that damage to the lungs was most relieved in the group injected with the mixed target antibody of G-CSF/M-CSF. In addition, as a result of conducting an experiment which confirmed whether the accumulation of collagen, which is a major extracellular matrix constituent, was decreased in a normal group, a pulmonary fibrotic group by exposure to radiation and groups injected with G-CSF/M-CSF single and mixed target antibodies, it was confirmed that the collagen increased by exposure to radiation was further reduced in the group injected with the mixed target antibody compared to the groups injected with the single target antibody of G-CSF and M-CSF (see Example 5-1). Furthermore, as a result of conducting an experiment which compared the degree of expression of a gene associated with damage to the lungs for a pulmonary epithelial cell line group exposed to radiation and groups injected with a single target antibody or mixed target antibody of M-CSF and G-CSF, it was confirmed that the expression of α-smooth muscle actin (α-SMA) and collagen was further greatly decreased in the group injected with the mixed target antibody of G-CSF/M-CSF compared to the groups injected with the single target antibody of G-CSF, M-CSF and GM-CSF, and it was confirmed that the application of the mixed target antibody of G-CSF/M-CSF to the pulmonary epithelial cell line exposed to radiation had a preventive and therapeutic effect on fibrotic diseases (see Example 5-2).

The above results suggest the use of one or more markers selected from the group consisting of M-CSF and G-CSF in diagnosing the development and progression of pulmonary fibrosis, and suggests that the mixed target antibody of M-CSF and G-CSF may be usefully used as a prophylactic or therapeutic agent for pulmonary fibrosis by inhibiting an epithelial to mesenchymal transition regulator and an extracellular matrix constituent factor to reduce the epithelial to mesenchymal transition of pulmonary epithelial cells and the accumulation of the extracellular matrix.

The composition according to the present disclosure comprises an anti-M-CSF antibody and an anti-G-CSF antibody as active ingredients, and may also comprise a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, granules, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in Remington's literature. The pharmaceutical composition of the present disclosure is not particularly limited in formulation, but may be formulated into an injection, an inhalant, an external preparation for skin, an oral ingestant, or the like.

The composition of the present disclosure may be orally administered or may be parenterally administered (for example, administered intravenously, subcutaneously, and through the skin, the nasal cavity, or the respiratory tract) according to the target method, and the administration dose may vary depending on the patient's condition and body weight, severity of disease, drug form, and administration route and period, but may be appropriately selected by the person skilled in the art.

The composition of the present disclosure is administered in a pharmaceutically effective amount. In the present disclosure, "pharmaceutically effective amount" means an amount sufficient to treat diseases at a reasonable benefit/risk ratio applicable to medical treatment, and an effective dosage level may be determined according to factors including the type of diseases of patients, the severity of disease, the activity of drugs, sensitivity to drugs, administration time, administration route, excretion rate, treatment period, and simultaneously used drugs, and other factors well known in the medical field. The composition according to the present disclosure may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

Specifically, the effective amount of the composition according to the present disclosure may vary depending on the patient's age, sex, and body weight, and generally, 0.001 to 150 mg of the composition and preferably, 0.01 to 100 mg of the composition, per 1 kg of the body weight, may be administered daily or every other day or may be administered once to three times a day. However, since the preferred dosage may be increased or decreased depending on the administration route, the severity of pulmonary fibrosis, the gender, the body weight, the age, and the like, the preferred dosage is not intended to limit the scope of the present disclosure in any way.

Meanwhile, as another aspect of the present disclosure, the present disclosure provides a method for preventing, regulating or treating pulmonary fibrosis, the method comprising administering the composition to a subject.

As used herein, the term "prevention" refers to all actions that inhibit pulmonary fibrosis or delay the development of pulmonary fibrosis by administering the composition according to the present disclosure.

As used herein, the term "treatment" refers to all actions in which symptoms of pulmonary fibrosis are ameliorated or beneficially altered by administering the composition according to the present disclosure.

As used herein, the "subject" refers to a subject in need of prevention, regulation or treatment of a disease, and more specifically, refers to a mammal such as a human or a non-human primate, a mouse, a rat, a dog, a cat, a horse, and a cow.

Hereinafter, preferred examples for helping the understanding of the present disclosure will be suggested. However, the following examples are provided only to more easily understand the present disclosure, and the contents of the present disclosure are not limited by the following examples.

EXAMPLES

Example 1. Experimental Preparation and Experimental Methods

1-1. Preparation of Pulmonary Epithelial Cells and Mononuclear Cells

After pulmonary epithelial cells BEAS-2B (human bronchial epithelial cell line), which are human pulmonary tissue constituent cells, and a mononuclear cell line THP1 (Human Leukamic monocyte), which is a type of human leukocyte, were obtained in a frozen state from the Korean Cell Line Bank (https://cellbank.snu.ac.kr/), the cells were cultured using a RPMI 1640 culture medium manufactured by Gibco™ Invitrogen Corporation. In this case, as a cell culture medium, a mixture of 10% fetal bovine serum (FBC) and 1% antibiotic was used.

In addition, this experiment is intended to evaluate cytological effects by external stimuli as part of a reproducibility experiment of cell damage by radiation after radiation therapy, and when patients with lung cancer and breast cancer receive radiation therapy for curative treatment purposes, epithelial cells, endothelial cells, fibrous cells, and the like in a tissue are stimulated and damaged by radiation, and in this case, cells produce various inflammatory mediators in order to address the damage to various organs, thereby promoting cell differentiation, acquisition of mobility and secretion of various extracellular matrix constituent factors. In order to reproduce the series of reactions described above, a special purpose three-dimensional culture structure (Transwell insert) comprising THP1 and pulmonary epithelial cells was utilized.

1-2. Preparation of Experimental Animal Model

C57BL/6J was purchased from Central Lab. Animal Inc., and then subjected to a one-week acclimatization period to stabilize the experimental animals. The chest was then locally irradiated with radiation at an intensity of 12.5 Gy. This experiment preparation is intended to evaluate the effect of exposure to radiation on the degree of fibrosis in pulmonary tissue as part of a reproduction experiment to build a model for damage to the lungs according to side effects of local radiation therapy used for curative purposes.

1-3. Immunochemical (Fluorescent) Staining for Epithelial to Mesenchymal Transition and Detection of Extracellular Matrix Activity Immunochemical staining is used for specific diagnosis of a specific disease associated with genes using antibodies against proteins generated by causal factors and stimuli, and is an experimental method performed to observe gene and protein distribution and expression. Antigen-antibody immunochemical cell staining and tissue staining were performed to evaluate the degree of the epithelial-mesenchymal transition of pulmonary cells and tissues by exposure to radiation and mutual remodeling activity with extracellular matrix constituent elements.

In general, when these activities are confirmed at the cell or tissue level, primary and secondary antibodies are used to detect the presence of specific proteins in specific cells and tissues. That is, the primary antibody has a high affinity for a specific protein as an antibody protein for detecting the specific protein, and the secondary antibody is not only used to detect the primary antibody but also may indicate the distribution of the specific protein. During observation, a fluorescent protein is used to expand and induce the expression signal of a specific protein or to classify the expression signal with a specific color. For example, fluorescein isothiocyanate (FITC) may be used for labeling and detection with an antibody protein with a green wavelength, cyanine-3 (Cy3) may be used for an antibody protein with a red wavelength, and an antigen may be localized by binding to horseradish peroxidase (HRP) and staining with the 3,3'-diaminobenzidine (DAB) reaction.

α-smooth muscle actin (α-SMA), which is a marker for myofibroblasts, and collagen were used as primary antibodies to confirm the degree of the corresponding myofibroblast hyperplasia or pulmonary fibrosis, and surface antibodies N-cadherin, E-cadherin, fibronectin, vimentin, and Snail and transcriptional regulatory proteins Snail and Zeb1 were used to confirm the epithelial to mesenchymal transition.

In addition, in order to detect mutual regulation and remodeling activity with extracellular matrix constituent elements around pulmonary epithelial cells, pulmonary fibrosis-related experiments were performed using osteopontin (OPN), which is a main cytoskeleton protein, versican, and hyaluronan synthase (HAS3), which is a major collagen synthesis factor. The dilution ratios used for the reaction of the antibodies used for the immunochemical staining were 1:100 to 1:200, and as a dilution medium, a 1% bovine serum albumin solution was used.

1-4. Quantitative Polymerase Chain Reaction

A real-time polymerase chain reaction is a technique of simultaneously amplifying a target DNA molecule and measuring the amount of target DNA molecule, and is an experimental technique of measuring the absolute number of replications of a targeted gene or a relative amount of the targeted gene.

After cells and tissues which caused myofibroblast hyperplasia or pulmonary fibrosis were extracted, DNA, RNA, and proteins in the cells/tissues were separated using TRIzol. Then, the cells/tissues were centrifuged, a RNA layer was separated, and then only RNA was purified by mixing chloroform. Pure RNA obtained after the purification and a washing process was quantified in an amount of 100 ng and synthesized into cDNA. Using the synthesized DNA as a template, the primers of the targeted gene were introduced together, and through the processes of denaturation, annealing, and elongation, it was confirmed whether the amplification of the targeted gene actually caused a reaction. The human gene sequence having the same name as the antibody used in Example 1-1 was custom-made and used, and the used primers are as follows.

The primers used in FIGS. 3 and 22 are mouse genes, and as shown in Table 1 below, the primers were used in experiments on pulmonary tissues of experimental animals that had myofibroblast hyperplasia or pulmonary fibrosis due to exposure to radiation (All primer sequences are described based on 5'->3').

TABLE 1

| Classification | Forward Primer (forward) | Reverse Primer (reverse) |
|---|---|---|
| α-SMA | TCAGCGCCTCCAGT TCCT (SEQ ID NO: 1) | AAAAACCACGAGTA ACAAATCAA (SEQ ID NO: 2) |
| collagen | ATGTCGCTATCCAG CTGACCTT (SEQ ID NO: 3) | GATGACTGTCTTGC CCCAAGTT (SEQ ID NO: 4) |

The primers used in FIGS. 8 and 23 are mouse genes, and as shown in Table 2 below, the primers were used in experiments on pulmonary tissues of experimental animals that had myofibroblast hyperplasia or pulmonary fibrosis due to exposure to radiation.

TABLE 2

| Classification | Forward Primer (forward) | Reverse Primer (reverse) |
|---|---|---|
| N-CAD | ATGTGCCGGATAGC GGGAGC (SEQ ID NO: 5) | TACACCGTGCCGTC CTCGTC (SEQ ID NO: 6) |
| E-cad | CACCTGGAGAGAGG CCATGT (SEQ ID NO: 7) | TGGGAAACATGAGC AGCTCT (SEQ ID NO: 8) |
| Fibronectin | AGGGAAACACAGGT AGCCAA (SEQ ID NO: 9) | AAGTGAGTTCTGTG GGAGGG (SEQ ID NO: 10) |
| VIM | GGGTGAGTAGAGAG TTCGGC (SEQ ID NO: 11) | GACCCGGAAAGAAG TGAGGA (SEQ ID NO: 12) |
| Snail | AAGATGCACATCCG AAGCCA (SEQ ID NO: 13) | CTCTTGGTGCTTGT GGAGCA (SEQ ID NO: 14) |
| Zeb | GATCGCCGATTCTG TGAACC (SEQ ID NO: 15) | TTCCTGGGGCTCAT TTCCAT (SEQ ID NO: 16) |

The primers used in FIGS. 10 and 24 are mouse genes, and as shown in Table 3 below, the primers were used in experiments on pulmonary tissues of experimental animals that had myofibroblast hyperplasia or pulmonary fibrosis due to exposure to radiation.

TABLE 3

| Classification | Forward Primer (forward) | Reverse Primer (reverse) |
|---|---|---|
| Versican | ACCAGACATGCTTC CCTCTC (SEQ ID NO: 17) | GTCACTGCACTGTA GGTCCT (SEQ ID NO: 18) |
| OPN | ATGCCACAGATGAG GACCTC (SEQ ID NO: 19) | CCTGGCTTCTTTGG ATGC (SEQ ID NO: 20) |
| HAS3 | CACACCAAAACATC CCAGGG (SEQ ID NO: 21) | ACCCTGACCCTCTC ATCTCT (SEQ ID NO: 22) |

The primers used in FIG. 12 are mouse genes, and as shown in Table 4 below, the primers were used in experiments on pulmonary tissues of experimental animals that had myofibroblast hyperplasia or pulmonary fibrosis due to exposure to radiation.

TABLE 4

| Classification | Forward Primer (forward) | Reverse Primer (reverse) |
|---|---|---|
| MCSF | CGAGTCAACAGAGC AACCAA (SEQ ID NO: 23) | GAGGGGGAAAACTT TGCTTC (SEQ ID NO: 24) |
| GCSF | CTCAACTTTCTGCC CAGAGG (SEQ ID NO: 25) | TAGGTGGCACACAA CTGCTC (SEQ ID NO: 26) |

The primers used in FIG. 18 are human genes, and as shown in the following Table 5, were used to evaluate the direct activity of macrophages by exposure to radiation exposure.

TABLE 5

| Classification | Forward Primer (forward) | Reverse Primer (reverse) |
|---|---|---|
| MCSF | CCCCGTTTTAACTC CGTTCC (SEQ ID NO: 27) | TGTAGAACAAGAGG CCTCCG (SEQ ID NO: 28) |
| GCSF | CCCTCCCCATCCAT GTATT (SEQ ID NO: 29) | GATGGGAGGACAGG AGCTTT (SEQ ID NO: 30) |
| α-SMA | GTTTGGGAAAGTGG GAG (SEQ ID NO: 31) | CATTGTCACACACC AAGGCA (SEQ ID NO: 32) |
| TREM | CTCAGTCTGCTCCT GGAACA (SEQ ID NO: 33) | TATCCGAAAGTGCC CAGTGT (SEQ ID NO: 34) |
| iNOS | ACAAGCCTACCCCT CCAGAT (SEQ ID NO: 35) | TCCCGTCAGTTGGT AGGTTC (SEQ ID NO: 36) |
| CXCL10 | CTGTACGCTGTACC TGCATCA (SEQ ID NO: 37) | TTCTTGATGGCCTT CGATTC (SEQ ID NO: 38) |
| CCL2 | GCTCAGCCAGATGC AATCAA (SEQ ID NO: 39) | ACAGATCTCCTTGG CCACAA (SEQ ID NO: 40) |

Example 2. Changes in Normal Pulmonary Epithelial Cells Exposed to Radiation

2-1. Confirmation of Differentiation of Normal Pulmonary Epithelial Cells Into Myofibroblasts and Collagen Accumulation A BEAS-2B cell line (human bronchial epithelial cell line), which is a human bronchial epithelial cell, was irradiated with radiation at an intensity of 2 Gy per day for 3 days. This experiment is intended to evaluate the cytological effects of radiation as part of a reproduction experiment of radiation therapy. FIG. 1 illustrates an experimental design of the aforementioned irradiation with radiation.

As a result, it was confirmed that the accumulation of α-smooth muscle actin (α-SMA), which is a marker for myofibroblasts, and intracellular collagen was increased in epithelial cells exposed to radiation.

In addition, as illustrated in FIG. 2, it was confirmed that the accumulation of α-smooth muscle actin (α-SMA) and collagen was increased in epithelial cells exposed to radiation using a surface antigen marker.

Furthermore, as illustrated in FIG. 3, it was confirmed that the accumulation of α-smooth muscle actin (α-SMA) and collagen was increased in epithelial cells exposed to radiation by comparing the amounts of mRNA before and after irradiation with radiation.

2-2. Confirmation of Differentiation Into Myofibroblasts and Collagen Accumulation in Experimental Animal Model In order to evaluate the direct effects of local radiation exposure, it was confirmed whether this experimental result coincided with the experimental results in Example 2-1 by using an experimental animal model to irradiate the model with radiation at an intensity of 12.5 Gy and removing pulmonary parenchymal tissue after 1, 4, 16, 19 and 27 weeks to track the degree of pulmonary fibrosis by HE staining, Sirius red staining and Masson's trichrome staining. FIG. 4 illustrates an experimental plan for local irradiation of an experimental animal model with radiation.

As a result, as illustrated in FIG. 5, it was confirmed by HE staining that the formation of pulmonary fibroblastic foci and the structural deformity of the lungs increased remarkably as time elapsed after local exposure to radiation. In addition, an increase in collagen accumulation and an increase in fibrous cells and collagenous cells were confirmed by Sirius red staining and Masson's trichrome staining.

Furthermore, an experiment was conducted to confirm whether the proliferation of myofibroblasts and the accumulation of collagen were increased using a surface antigen marker.

As a result, as illustrated in FIG. 6, from an increase in α-smooth muscle actin (α-SMA) the hyperactive proliferation of myofibroblasts was confirmed, and an increase in accumulation of collagen was confirmed.

From the aforementioned experimental results, it was confirmed that specific mediators were activated by stimulation and damage of pulmonary epithelial cells by exposure to radiation, and accordingly, normal pulmonary epithelial cells differentiated into myofibroblasts and the secretion of collagen, which is the main material of the extracellular matrix, was increased.

Example 3. Epithelial to Mesenchymal Transition and Extracellular Matrix Remodeling as Pulmonary Fibrosis Progresses An experiment was conducted to confirm the presence or absence of the epithelial to mesenchymal transition and whether extracellular matrix remodeling occurred by extracting a pulmonary parenchymal tissue of an experimental animal model in which fibrosis was induced.

3-1. Confirmation of Progression of Epithelial to Mesenchymal Transition

An experiment was conducted to confirm the presence or absence of the epithelial to mesenchymal transition by extracting a pulmonary parenchymal tissue of an experimental animal model in which fibrosis was induced.

As a result, as illustrated in FIG. 7, it was confirmed that the expression of markers (fibronectin, vimentin) and a regulator (ZEB1) for the epithelial to mesenchymal transition was greatly increased as fibrosis progressed.

Further, the degrees of expression of the above factors were compared by comparing the amounts of mRNAs extracted from the corresponding tissues.

As a result, as illustrated in FIG. 8, it was confirmed that the expression of markers (fibronectin, vimentin) and a regulator (ZEB1) for the epithelial to mesenchymal transition was increased. Except for the above factors, it was confirmed that after irradiation with radiation, the expression level of E-Cad was decreased and the expression levels of N-Cad and Snail were increased.

3-2. Confirmation of Progression of Extracellular Matrix Remodeling

An experiment was conducted to confirm whether the extracellular matrix was increased by extracting a pulmonary parenchymal tissue of an experimental animal model in which fibrosis was induced.

As a result, as illustrated in FIG. 9, it was confirmed that the expression of various marker factors (versican, OPN) for extracellular matrix constituent elements and a main factor (HAS3) for collagen synthesis in pulmonary fibrotic tissue was increased, and as illustrated in images at 4 and 27 weeks in FIG. 9, it was confirmed that extracellular matrix remodeling occurred.

Further, the degrees of expression of the above factors were compared by comparing the amounts of mRNAs extracted from the corresponding tissues.

As a result, as illustrated in FIG. 10, it was confirmed that the expression of various marking factors (versican, OPN) for extracellular matrix constituent elements and a main factor (HAS3) for collagen synthesis in pulmonary fibrotic tissue was increased.

From the above experimental results, it was confirmed that the epithelial to mesenchymal transition and extracellular matrix remodeling (ECM remodeling) of various cells in the pulmonary tissue occurred as the pulmonary fibrosis due to radiation progressed.

Example 4. Mechanism of Action of M-CSF and G-CSF in Pulmonary Fibrosis

4-1. Cytokine Array of Pulmonary Parenchymal Tissue Exposed to Radiation

When stimulation and damage to cells are induced by radiation, cells activate a recovery mechanism through cell differentiation, the epithelial to mesenchymal transition, and interactions with extracellular matrix constituent components as a defense mechanism to repair the damage.

In this case, in order to confirm what material is involved in the recovery mechanism, an experiment for screening inflammatory active factors was conducted on a pulmonary parenchymal tissue in which damage was induced by radiation.

As a result, as illustrated in FIG. 11, it was confirmed that M-CSF (CSF type 1) and G-CSF (CSF type 3) were increased together with IL-6, IL-8 and TGF-β1 which are commonly secreted in various fibrotic cells. However, since IL-6 and IL-8TGF-β1 are already known as inducers or mediators of various fibrotic diseases and are affected by various signal transductions, IL-6 and IL-8TGF-β1 were not targeted because it is not desirable to employ IL-6 and IL-8TGF-β1 as a target for treatment of a disease.

In addition, the degrees of expression of the above materials were compared by comparing the amounts of mRNAs extracted from pulmonary parenchymal tissues in which damage was induced by radiation.

As a result, as illustrated in FIG. 12, it was confirmed that the expression of M-CSF and G-CSF was greatly increased as time elapsed. Furthermore, as illustrated in FIG. 13, it was confirmed that the expression of M-CSF and G-CSF was increased as the pulmonary fibrosis damage worsened. This confirms that M-CSF and/or G-CSF has a marker use in diagnosing the development and progression of pulmonary fibrosis.

4-2. Increase in Expression of M-CSF and G-CSF and Increase in Expression of α-Smooth Muscle Actin (α-SMA) and Collagen An experiment was conducted to confirm whether the expression of myofibroblasts and collagen was increased when the expression of M-CSF and G-CSF was increased.

As a result, as illustrated in FIG. 14 or FIG. 15, it was confirmed that the expression of α-smooth muscle actin (α-SMA), which is a marker for myofibroblasts, and collagen, which is a main constituent for the extracellular matrix, was increased along with an increase in M-CSF and G-CSF.

4-3. Increase in Expression of M-CSF and G-CSF and Recruitment of Macrophages M-CSF and G-CSF are known as mediators which help the growth and activity of immune cells in the body. Further, as illustrated in FIG. 16, since it was confirmed that macrophages infiltrated into a tissue with weakened pulmonary fibrosis, an experiment was conducted to visually confirm macrophage recruitment, which is mediated by M-CSF and G-CSF, in pulmonary parenchymal tissue.

As a result, as illustrated in FIG. 17, it was confirmed that the aggregation of macrophages was increased as the expression of M-CSF and G-CSF was increased.

Thus, as it was necessary to confirm the expression levels of the active factors and secretory factors of the macrophages themselves with increased aggregation, an experiment was conducted to confirm the degree of expression of the above factors by measuring the mRNA expression level.

As a result, as illustrated in FIG. 18, it was confirmed that the expression of an immune cell activity assessment factor (TRM1), anti-inflammatory macrophage secretory factors (iNOS, CXCL10), and a non-immunized macrophage secretory factor (CCL2) was increased along with M-CSF, G-CSF, α-smooth muscle actin (α-SMA), and collagen.

From the above experimental results, it was confirmed that the secretory factors increased by radiation damage induce the differentiation of the cells themselves, and simultaneously repair the damage or worsens the fibrotic disease by recruiting and differentiating macrophages circulating in the extracellular matrix.

Example 5. Confirmation of Therapeutic Effect on Pulmonary Fibrosis Using Target Antibody

5-1. Therapeutic Effect of Target Antibodies of M-CSF (Single), G-CSF (Single), and M-CSF/G-CSF (Mixed) on Pulmonary Fibrosis The chest of the experimental animal model was exposed to radiation at an intensity of 12.5 Gy, and after 24 hours, target antibodies of M-CSF (single), G-CSF (single), and M-CSF/G-CSF (mixed) were injected intraperitoneally at a concentration of 250 ug/kg for 3 days. Parenchymal pulmonary tissues were analyzed 1 week, 4 weeks, 16 weeks, 19 weeks and 27 weeks after the above target antibodies were injected. FIG. 19 illustrates an experimental design of the aforementioned irradiation with radiation. Specifically, therapeutic effects were confirmed for a normal group, a pulmonary tissue fibrosis group due to exposure to radiation, and a group injected with a G-CSF/M-CSF single or mixed target antibody by pathological changes in pulmonary parenchymal tissue and changes in gene expression patterns.

As a result, as illustrated in FIG. 20, it was confirmed that fibroblastic foci were greatly increased in a site around the lungs and a normal site of the group which was exposed to radiation and not injected with the target antibody, and irreparable structural damage to the lungs occurred.

However, it was confirmed that a group in which the antibody was injected with G-CSF and M-CSF as single or mixed targets greatly reduced the degree of damage to the lungs caused by radiation, and in particular, it was confirmed that damage to the lungs was most relieved in the group injected with the mixed target antibody of G-CSF/M-CSF.

In addition, an experiment was conducted to confirm whether the accumulation of collagen, which is a main element constituting the extracellular matrix, was decreased in the normal group, the pulmonary tissue fibrosis group due to exposure to radiation, and the group injected with G-CSF/M-CSF single or mixed target antibody.

As a result, as illustrated in FIG. 21, it was confirmed that collagen increased by exposure to radiation was decreased most in the group injected with the mixed target antibody of G-CSF/M-CSF compared to the group injected with the single target antibody of G-CSF and M-CSF.

Furthermore, an experiment was performed to compare the degrees of gene expression associated with damage to the lungs in the normal group, the pulmonary tissue fibrosis group due to exposure to radiation, and the group injected with the G-CSF/M-CSF single or mixed target antibody.

As a result, as illustrated in FIG. 22, it was confirmed that in the group injected with a single target antibody or mixed target antibody of M-CSF and G-CSF, active secretory factors (M-CSF, G-CSF, α-SMA, and collagen) increased by radiation damage were decreased. Further, as illustrated in FIG. 23, it was confirmed that regulators vimentin, ZEB1) for the epithelial to mesenchymal transition were decreased. In addition, as illustrated in FIG. 24, it was confirmed that the extracellular matrix constituent factors (versican, HAS3) were greatly decreased. In particular, it was confirmed that the expression of the above factors was greatly decreased in the group injected with the mixed target antibody.

5-2. Therapeutic Effect of Target Antibodies of M-CSF (Single), G-CSF (Single), GM-CSF (Single), and M-CSF/G-CSF (Mixed) on Pulmonary Fibrosis An experiment was performed to compare the degrees of expression of genes associated with damage to the lungs in a pulmonary epithelial cell line group exposed to radiation at an intensity of 6 Gy and a group injected with a single target antibody or mixed target antibody of M-CSF and G-CSF in the pulmonary epithelial cell line exposed to radiation at an intensity of 6 Gy.

As a result, as illustrated in FIG. 25, it was confirmed that the expression of α-smooth muscle actin (α-SMA) and collagen was further greatly decreased in the group injected with the mixed target antibody of G-CSF/M-CSF compared to the group injected with the single target antibody of G-CSF, M-CSF, and GM-CSF.

In addition, pulmonary epithelial cells were respectively set at $3\times10^5$, irradiated with radiation at an intensity of 6 Gy, and then immediately treated with G-CSF/M-CSF mixed target antibodies having various ratios (G-CSF/M-CSF=7/3, 5/5, 3/7), and 48 hours was allowed to elapse.

As a result, as illustrated in FIG. 26, it was confirmed that the expression of α-smooth muscle actin (α-SMA) and collagen was decreased in all the groups injected with the mixed target antibody of G-CSF/M-CSF compared to the control (experimental group irradiated with radiation and not treated with an antibody).

Furthermore, pulmonary epithelial cells were respectively set at $2\times10^5$, irradiated with radiation at an intensity of 6 Gy, and then treated with the mixed target antibody of G-CSF/M-CSF after 24 hours, and 48 hours was allowed to elapse.

As a result, as illustrated in FIG. 26, it was confirmed that the expression of α-smooth muscle actin (α-SMA) and collagen was decreased in the group injected with the mixed target antibody of G-CSF/M-CSF compared to the control (experimental group irradiated with radiation and not treated with an antibody).

From the above experimental results, it was confirmed that a combined target antibody therapeutic therapy had a greater therapeutic effect on pulmonary fibrosis than a single target antibody therapeutic therapy. Further, it was confirmed that application of the mixed target antibody of M-CSF and G-CSF could prevent and treat the corresponding disease by fundamentally inactivating mediators (M-CSF, G-CSF) increased by tissue damage caused by radiation to inhibit differentiation into myofibroblasts and accumulation of the extracellular matrix, thereby enabling a series of fibrotic chain reactions to be controlled.

The above-described description of the present disclosure is provided for illustrative purposes, and a person skilled in the art to which the present disclosure pertains will understand that the present disclosure can be easily modified into other specific forms without changing the technical spirit or essential features of the present disclosure. Therefore, it should be understood that the above-described examples are only illustrative in all aspects and not restrictive.

INDUSTRIAL APPLICABILITY

The present disclosure relates to a marker composition for diagnosing the development or progression of pulmonary fibrosis, comprising M-CSF and/or G-CSF, and to a composition for preventing or treating pulmonary fibrosis, comprising an anti-M-CSF target antibody and an anti-G-CSF target antibody, the development or progression of pulmonary fibrosis can be diagnosed by measuring the expression level of M-CSF and/or G-CSF, and the antibodies can prevent or treat pulmonary fibrosis by inhibiting M-CSF and G-CSF to decrease factors associated with differentiation into myofibroblasts, the epithelial to mesenchymal transition, and extracellular matrix remodeling, and thus can be used in the related diagnostic and therapeutic industries by dramatically enhancing the diagnostic and therapeutic efficacy of pulmonary fibrosis.

The invention claimed is:

1. A method for treating pulmonary fibrosis in a subject in need thereof, the method comprising administering an effective amount of a composition comprising an anti-macrophage-colony stimulating factor (M-CSF) antibody and an anti-granulocyte-colony stimulating factor (G-CSF) antibody as active ingredients to the subject.

2. The method according to claim 1, wherein the pulmonary fibrosis is induced by irradiation with radiation.

3. The method according to claim 1, wherein the pulmonary fibrosis comprises myofibroblast hyperplasia or pulmonary fibrosis of pulmonary cells.

4. The method according to claim 1, wherein the composition inhibits differentiation of pulmonary cells into myofibroblasts.

5. The method according to claim 1, wherein the composition inhibits the epithelial to mesenchymal transition (EMT).

6. The method according to claim 1, wherein the composition inhibits extracellular matrix remodeling (ECM remodeling).

7. The method according to claim 4, wherein the inhibition of differentiation into myofibroblasts inhibits the expression of α-smooth muscle actin (α-SMA).

8. The method according to claim 5, wherein the inhibition of the epithelial to mesenchymal transition inhibits the expression of one or more proteins selected from the group consisting of fibronectin (FN), vimentin (VIM), and ZEB1.

9. The method according to claim 6, wherein the inhibition of extracellular matrix remodeling inhibits the expression of one or more proteins selected from the group consisting of versican, osteopontin (OPN), collagen, and HAS3.

* * * * *

SEQUENCE LISTING

```
<160> NUMBER OF SEQ ID NOS: 40

<210> SEQ ID NO 1
<211> LENGTH: 18
<212> TYPE: DNA
<213> ORGANISM: Artificial Sequence
<220> FEATURE:
<223> OTHER INFORMATION: alpha-SMA forward primer in table 1

<400> SEQUENCE: 1
```

```
tcagcgcctc cagttcct                                                    18


<210> SEQ ID NO 2
<211> LENGTH: 23
<212> TYPE: DNA
<213> ORGANISM: Artificial Sequence
<220> FEATURE:
<223> OTHER INFORMATION: alpha-SMA reverse primer in table 1

<400> SEQUENCE: 2

aaaaaccacg agtaacaaat caa                                              23


<210> SEQ ID NO 3
<211> LENGTH: 22
<212> TYPE: DNA
<213> ORGANISM: Artificial Sequence
<220> FEATURE:
<223> OTHER INFORMATION: collagen forward primer

<400> SEQUENCE: 3

atgtcgctat ccagctgacc tt                                               22


<210> SEQ ID NO 4
<211> LENGTH: 22
<212> TYPE: DNA
<213> ORGANISM: Artificial Sequence
<220> FEATURE:
<223> OTHER INFORMATION: collagen reverse primer

<400> SEQUENCE: 4

gatgactgtc ttgccccaag tt                                               22


<210> SEQ ID NO 5
<211> LENGTH: 20
<212> TYPE: DNA
<213> ORGANISM: Artificial Sequence
<220> FEATURE:
<223> OTHER INFORMATION: N-CAD forward primer

<400> SEQUENCE: 5

atgtgccgga tagcgggagc                                                  20


<210> SEQ ID NO 6
<211> LENGTH: 20
<212> TYPE: DNA
<213> ORGANISM: Artificial Sequence
<220> FEATURE:
<223> OTHER INFORMATION: N-CAD reverse primer

<400> SEQUENCE: 6

tacaccgtgc cgtcctcgtc                                                  20


<210> SEQ ID NO 7
<211> LENGTH: 20
<212> TYPE: DNA
<213> ORGANISM: Artificial Sequence
<220> FEATURE:
<223> OTHER INFORMATION: E-cad forward primer

<400> SEQUENCE: 7

cacctggaga gaggccatgt                                                  20


<210> SEQ ID NO 8
<211> LENGTH: 20
<212> TYPE: DNA
```

<213> ORGANISM: Artificial Sequence
<220> FEATURE:
<223> OTHER INFORMATION: E-cad reverse primer

<400> SEQUENCE: 8
tgggaaacat gagcagctct 20

<210> SEQ ID NO 9
<211> LENGTH: 20
<212> TYPE: DNA
<213> ORGANISM: Artificial Sequence
<220> FEATURE:
<223> OTHER INFORMATION: Fibronectin forward primer

<400> SEQUENCE: 9
agggaaacac aggtagccaa 20

<210> SEQ ID NO 10
<211> LENGTH: 20
<212> TYPE: DNA
<213> ORGANISM: Artificial Sequence
<220> FEATURE:
<223> OTHER INFORMATION: Fibronectin reverse primer

<400> SEQUENCE: 10
aagtgagttc tgtgggaggg 20

<210> SEQ ID NO 11
<211> LENGTH: 20
<212> TYPE: DNA
<213> ORGANISM: Artificial Sequence
<220> FEATURE:
<223> OTHER INFORMATION: VIM forward primer

<400> SEQUENCE: 11
gggtgagtag agagttcggc 20

<210> SEQ ID NO 12
<211> LENGTH: 20
<212> TYPE: DNA
<213> ORGANISM: Artificial Sequence
<220> FEATURE:
<223> OTHER INFORMATION: VIM reverse primer

<400> SEQUENCE: 12
gacccggaaa gaagtgagga 20

<210> SEQ ID NO 13
<211> LENGTH: 20
<212> TYPE: DNA
<213> ORGANISM: Artificial Sequence
<220> FEATURE:
<223> OTHER INFORMATION: Snail forward primer

<400> SEQUENCE: 13
aagatgcaca tccgaagcca 20

<210> SEQ ID NO 14
<211> LENGTH: 20
<212> TYPE: DNA
<213> ORGANISM: Artificial Sequence
<220> FEATURE:
<223> OTHER INFORMATION: Snail reverse primer

<400> SEQUENCE: 14
ctcttggtgc ttgtggagca 20

<210> SEQ ID NO 15
<211> LENGTH: 20
<212> TYPE: DNA
<213> ORGANISM: Artificial Sequence
<220> FEATURE:
<223> OTHER INFORMATION: Zeb forward primer

<400> SEQUENCE: 15
gatcgccgat tctgtgaacc 20

<210> SEQ ID NO 16
<211> LENGTH: 20
<212> TYPE: DNA
<213> ORGANISM: Artificial Sequence
<220> FEATURE:
<223> OTHER INFORMATION: Zeb reverse primer

<400> SEQUENCE: 16
ttcctggggc tcatttccat 20

<210> SEQ ID NO 17
<211> LENGTH: 20
<212> TYPE: DNA
<213> ORGANISM: Artificial Sequence
<220> FEATURE:
<223> OTHER INFORMATION: Versican forward primer

<400> SEQUENCE: 17
accagacatg cttccctctc 20

<210> SEQ ID NO 18
<211> LENGTH: 20
<212> TYPE: DNA
<213> ORGANISM: Artificial Sequence
<220> FEATURE:
<223> OTHER INFORMATION: Versican reverse primer

<400> SEQUENCE: 18
gtcactgcac tgtaggtcct 20

<210> SEQ ID NO 19
<211> LENGTH: 20
<212> TYPE: DNA
<213> ORGANISM: Artificial Sequence
<220> FEATURE:
<223> OTHER INFORMATION: OPN forward primer

<400> SEQUENCE: 19
atgccacaga tgaggacctc 20

<210> SEQ ID NO 20
<211> LENGTH: 18
<212> TYPE: DNA
<213> ORGANISM: Artificial Sequence
<220> FEATURE:
<223> OTHER INFORMATION: OPN reverse primer

<400> SEQUENCE: 20
cctggcttct ttggatgc 18

<210> SEQ ID NO 21
<211> LENGTH: 20
<212> TYPE: DNA
<213> ORGANISM: Artificial Sequence
<220> FEATURE:

<223> OTHER INFORMATION: HAS3 forward primer

<400> SEQUENCE: 21
cacaccaaaa catcccaggg 20

<210> SEQ ID NO 22
<211> LENGTH: 20
<212> TYPE: DNA
<213> ORGANISM: Artificial Sequence
<220> FEATURE:
<223> OTHER INFORMATION: HAS3 reverse primer

<400> SEQUENCE: 22
accctgaccc tctcatctct 20

<210> SEQ ID NO 23
<211> LENGTH: 20
<212> TYPE: DNA
<213> ORGANISM: Artificial Sequence
<220> FEATURE:
<223> OTHER INFORMATION: MCSF forward primer in table 4

<400> SEQUENCE: 23
cgagtcaaca gagcaaccaa 20

<210> SEQ ID NO 24
<211> LENGTH: 20
<212> TYPE: DNA
<213> ORGANISM: Artificial Sequence
<220> FEATURE:
<223> OTHER INFORMATION: MCSF reverse primer in table 4

<400> SEQUENCE: 24 gaggggaaa actttgcttc 20

<210> SEQ ID NO 25
<211> LENGTH: 20
<212> TYPE: DNA
<213> ORGANISM: Artificial Sequence
<220> FEATURE:
<223> OTHER INFORMATION: GCSF forward primer in table 4

<400> SEQUENCE: 25
ctcaactttc tgcccagagg 20

<210> SEQ ID NO 26
<211> LENGTH: 20
<212> TYPE: DNA
<213> ORGANISM: Artificial Sequence
<220> FEATURE:
<223> OTHER INFORMATION: GCSF reverse primer in table 4

<400> SEQUENCE: 26
taggtggcac acaactgctc 20

<210> SEQ ID NO 27
<211> LENGTH: 20
<212> TYPE: DNA
<213> ORGANISM: Artificial Sequence
<220> FEATURE:
<223> OTHER INFORMATION: MCSF forward primer in table 5

<400> SEQUENCE: 27
ccccgtttta actccgttcc 20

<210> SEQ ID NO 28
<211> LENGTH: 20
<212> TYPE: DNA
<213> ORGANISM: Artificial Sequence
<220> FEATURE:
<223> OTHER INFORMATION: MCSF reverse primer in table 5

<400> SEQUENCE: 28
tgtagaacaa gaggcctccg 20

<210> SEQ ID NO 29
<211> LENGTH: 19
<212> TYPE: DNA
<213> ORGANISM: Artificial Sequence
<220> FEATURE:
<223> OTHER INFORMATION: GCSF forward primer in table 5

<400> SEQUENCE: 29
ccctccccat ccatgtatt 19

<210> SEQ ID NO 30
<211> LENGTH: 20
<212> TYPE: DNA
<213> ORGANISM: Artificial Sequence
<220> FEATURE:
<223> OTHER INFORMATION: GCSF reverse primer in table 5

<400> SEQUENCE: 30
gatgggagga caggagcttt 20

<210> SEQ ID NO 31
<211> LENGTH: 17
<212> TYPE: DNA
<213> ORGANISM: Artificial Sequence
<220> FEATURE:
<223> OTHER INFORMATION: alpha-SMA forward primer in table 5

<400> SEQUENCE: 31
gtttgggaaa gtgggag 17

<210> SEQ ID NO 32
<211> LENGTH: 20
<212> TYPE: DNA
<213> ORGANISM: Artificial Sequence
<220> FEATURE:
<223> OTHER INFORMATION: alpha-SMA reverse primer in table 5

<400> SEQUENCE: 32
cattgtcaca caccaaggca 20

<210> SEQ ID NO 33
<211> LENGTH: 20
<212> TYPE: DNA
<213> ORGANISM: Artificial Sequence
<220> FEATURE:
<223> OTHER INFORMATION: TREM forward primer

<400> SEQUENCE: 33
ctcagtctgc tcctggaaca 20

<210> SEQ ID NO 34
<211> LENGTH: 20
<212> TYPE: DNA
<213> ORGANISM: Artificial Sequence
<220> FEATURE:
<223> OTHER INFORMATION: TREM reverse primer

<400> SEQUENCE: 34
tatccgaaag tgcccagtgt 20

<210> SEQ ID NO 35
<211> LENGTH: 20
<212> TYPE: DNA
<213> ORGANISM: Artificial Sequence
<220> FEATURE:
<223> OTHER INFORMATION: iNOS forward primer

<400> SEQUENCE: 35
acaagcctac ccctccagat 20

<210> SEQ ID NO 36
<211> LENGTH: 20
<212> TYPE: DNA
<213> ORGANISM: Artificial Sequence
<220> FEATURE:
<223> OTHER INFORMATION: iNOS reverse primer

<400> SEQUENCE: 36
tcccgtcagt tggtaggttc 20

<210> SEQ ID NO 37
<211> LENGTH: 21
<212> TYPE: DNA
<213> ORGANISM: Artificial Sequence
<220> FEATURE:
<223> OTHER INFORMATION: CXCL10 forward primer

<400> SEQUENCE: 37
ctgtacgctg tacctgcatc a 21

<210> SEQ ID NO 38
<211> LENGTH: 20
<212> TYPE: DNA
<213> ORGANISM: Artificial Sequence
<220> FEATURE:
<223> OTHER INFORMATION: CXCL10 reverse primer

<400> SEQUENCE: 38
ttcttgatgg ccttcgattc 20

<210> SEQ ID NO 39
<211> LENGTH: 20
<212> TYPE: DNA
<213> ORGANISM: Artificial Sequence
<220> FEATURE:
<223> OTHER INFORMATION: CCL2 forward primer

<400> SEQUENCE: 39
gctcagccag atgcaatcaa 20

<210> SEQ ID NO 40
<211> LENGTH: 20
<212> TYPE: DNA
<213> ORGANISM: Artificial Sequence
<220> FEATURE:
<223> OTHER INFORMATION: CCL2 reverse primer

<400> SEQUENCE: 40
acagatctcc ttggccacaa 20